(12) United States Patent
Bloch et al.

(10) Patent No.: US 10,603,150 B2
(45) Date of Patent: Mar. 31, 2020

(54) ORAL CARE IMPLEMENT

(71) Applicant: Colgate-Palmolive Company, New York, NY (US)

(72) Inventors: Brian Bloch, Hillsborough, NJ (US); Takahide Okai, Highland Park, NJ (US); John Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 133 days.

(21) Appl. No.: 15/838,709

(22) Filed: Dec. 12, 2017

(65) Prior Publication Data

US 2019/0175319 A1  Jun. 13, 2019

(51) Int. Cl.
| | | |
|---|---|---|
| *A61C 17/34* | (2006.01) | |
| *A61C 17/22* | (2006.01) | |
| *A46D 3/00* | (2006.01) | |
| *A46B 13/02* | (2006.01) | |
| *A46B 15/00* | (2006.01) | |

(52) U.S. Cl.
CPC ........ *A61C 17/3481* (2013.01); *A46B 13/023* (2013.01); *A46D 3/00* (2013.01); *A61C 17/222* (2013.01); *A46B 15/0081* (2013.01)

(58) Field of Classification Search
CPC ... A61C 17/34; A61C 17/3481; A61C 17/225; A61C 17/222; A46B 13/02; A46B 13/023; A46D 3/00
USPC .......................................................... 300/21
See application file for complete search history.

(56) References Cited

U.S. PATENT DOCUMENTS

| | | |
|---|---|---|
| 3,088,148 A | 5/1963 | Moret |
| 3,937,235 A | 2/1976 | Broughton |
| 5,617,601 A | 4/1997 | McDougall |
| 5,617,602 A | 4/1997 | Okada |
| 5,697,117 A | 12/1997 | Craft |
| 6,161,244 A | 12/2000 | Jeannet et al. |
| 6,836,917 B2 | 1/2005 | Blaustein et al. |
| 7,222,381 B2 | 5/2007 | Kraemer |
| 7,845,039 B2 | 12/2010 | Chan et al. |
| 8,453,285 B2 | 6/2013 | Dickie |
| 9,084,659 B2 | 7/2015 | Bovenkamp |
| 9,561,092 B2 * | 2/2017 | Sauer .................. A61C 17/222 |
| 2008/0020351 A1 | 1/2008 | Hilscher et al. |

(Continued)

FOREIGN PATENT DOCUMENTS

| | | |
|---|---|---|
| EP | 2478865 A1 | 7/2012 |
| WO | WO 2017095733 A1 | 11/2016 |

(Continued)

*Primary Examiner* — Laura C Guidotti

(57) ABSTRACT

An oral care implement including a handle and a replacement head that is detachably coupled to the handle. The handle may include a gripping portion extending from a proximal end to a distal end and a stem extending from the distal end of the gripping portion. The stem may have an inner cavity. A vibratory element including a motor and an eccentric may be partially located in the stem. The eccentric may have a first end that is operably coupled to the motor and a second end opposite the first end, the second end having an aperture therein. A guide pin may be fixed to the stem such that a first portion of the guide pin protrudes into the inner cavity of the stem. The first portion of the guide pin may extend through the aperture in the second end of the eccentric.

19 Claims, 16 Drawing Sheets

(56) References Cited

U.S. PATENT DOCUMENTS

| | | |
|---|---|---|
| 2008/0020352 A1 | 1/2008 | Hilscher et al. |
| 2011/0047729 A1 | 3/2011 | Iwahori et al. |
| 2014/0130274 A1 | 5/2014 | Fattori |
| 2014/0137346 A1 | 5/2014 | Fattori |
| 2014/0143963 A1 | 5/2014 | Fattori |
| 2014/0165312 A1 | 6/2014 | Fattori |
| 2014/0341636 A1 | 11/2014 | Fattori |
| 2015/0020325 A1 | 1/2015 | Yoshida et al. |
| 2017/0151044 A1 | 6/2017 | Okai |

FOREIGN PATENT DOCUMENTS

| | | |
|---|---|---|
| WO | WO 2017160811 A1 | 9/2017 |
| WO | WO 2017160816 A1 | 9/2017 |

\* cited by examiner

ORAL CARE IMPLEMENT

BACKGROUND

Myriad implements and devices for maintaining oral health are known. For example, toothbrushes of both the manual and powered variety, floss, dentifrices, applicators, agents, and the like are all known to provide different benefits in the oral cavity. The structure and function of such oral care implements are constantly being improved. For example, in powered oral care implements it is desirable to improve the seal between the replacement head and the handle to protect the electronic components thereof against water damage. Furthermore, it is also desirable to improve the ability of a vibratory element to impart vibrations to the cleaning elements. Additionally, it is desirable to simplify manufacture of such oral care implements by automating the process or making it easier to couple different components together to reduce manufacturing time and cost. Finally, improving the aesthetic design of such oral care implements facilitates an increase in sales. Thus, there is a need for improvement in all of the aforementioned areas with regard to oral care implements.

BRIEF SUMMARY

The present invention is directed to an oral care implement including a handle and a replacement head that is detachably coupled to the handle. The oral care implement may include a handle having a longitudinal axis that includes a gripping portion and a stem extending from the gripping portion. The gripping portion may have a shoulder that surrounds the stem and an annular rib protruding from the shoulder. The replacement head may have a sleeve portion terminating in a proximal edge that is formed from a resilient material. The replacement head may be detachably coupled to the handle so that the annular rib of the shoulder and the proximal edge of the sleeve portion that is formed of elastomeric material are in contact with one another.

In one aspect, the invention may be an oral care implement comprising: a handle having a longitudinal axis and comprising: a gripping portion extending from a proximal end to a distal end; and a stem extending from the distal end of the gripping portion, the gripping portion comprising a shoulder that surrounds the stem and an annular rib protruding from the shoulder; a replacement head comprising a sleeve portion having a cavity and an opening at a proximal edge of the sleeve portion, the proximal edge of the sleeve portion being formed from a resilient material; and wherein the replacement head is detachably coupled to the handle with the stem of the handle located within the cavity of the sleeve portion and the annular rib of the shoulder and the proximal edge of the sleeve portion in contact with one another.

In another embodiment, the invention may be an oral care implement comprising: a handle having a longitudinal axis and comprising a gripping portion extending from a proximal end to a distal end and a stem extending from the distal end of the gripping portion, the gripping portion comprising a shoulder that surrounds the stem; a replacement head comprising a sleeve portion having a cavity and an opening at a proximal edge of the sleeve portion; one of the proximal edge of the sleeve portion and the shoulder of the gripping portion comprising a resilient material; an annular rib protruding from one of the proximal edge of the sleeve portion and the shoulder of the gripping portion; and wherein the replacement head is detachably coupled to the handle with the stem of the handle located within the cavity of the sleeve portion and the proximal edge of the sleeve portion adjacent to the shoulder of the gripping portion so that the annular rib of the one of the proximal edge of the sleeve portion and the shoulder of the gripping portion is in direct surface contact with the other one of the proximal edge of the sleeve portion and the shoulder of the gripping portion.

In yet another embodiment, the invention may be an oral care implement comprising: a handle having a longitudinal axis and comprising: a gripping portion extending from a proximal end to a distal end; and a stem extending from the distal end of the gripping portion, the stem having an inner cavity defined by an inner surface and an upper wall of the stem; a vibratory element at least partially located in the stem and operably coupled to a power source, the vibratory element comprising a motor and an eccentric, the eccentric having a first end that is coupled to the motor and a second end opposite the first end, the second end comprising an aperture; a guide pin fixed to the stem, a first portion of the guide pin protruding from the upper wall and into the inner cavity of the stem and extending through the aperture in the second end of the eccentric; and a replacement head comprising a sleeve portion having a cavity, wherein the replacement head is detachably coupled to the handle with the stem of the handle located within the cavity of the sleeve portion.

In still another embodiment, the invention may be a handle for an electric toothbrush, the handle comprising: a gripping portion; a stem extending from the gripping portion, the stem comprising an inner cavity; a vibratory element at least partially located in the stem and operably coupled to a power source, the vibratory element comprising a motor and an eccentric, the eccentric having a first end that is coupled to the motor and a second end opposite the first end, the second end comprising an aperture; and a guide pin non-movably coupled to the stem, the guide pin comprising a first portion and a second portion, the second portion of the guide pin embedded within a wall of the stem and the first portion of the guide pin suspended within the inner cavity of the stem and extending through the aperture in the second end of the eccentric.

In a further embodiment, the invention may be a method of manufacturing a handle of an electric toothbrush, the method comprising: providing a gripping portion of the handle; providing a mold that defines a mold cavity, the mold cavity corresponding to a stem of the handle; supporting a second portion of a guide pin within the mold cavity; injecting a first material into the mold cavity so that the first material surrounds the second portion of the guide pin, wherein upon cooling the first material hardens to form the stem of the handle with the second portion of the guide pin being embedded within the stem and a first portion of the guide pin suspended within a cavity of the stem; inserting a vibratory element into the cavity of the stem until the first portion of the guide pin extends into an aperture in a distal end of the vibratory element; and coupling the stem to the gripping portion so that at least a portion of the stem extends from a distal end of the gripping portion.

In a still further embodiment, the invention may be a replacement head for detachable coupling to a handle of an oral care implement, the replacement head comprising: a head portion having a front surface with tooth cleaning elements extending therefrom; a sleeve portion comprising a cavity configured to receive a stem of the handle and a proximal edge defining an opening into the cavity, the sleeve portion comprising a first component formed of a rigid material and a second component formed of a resilient material; the first component of the sleeve portion comprising a locking element that is configured to mate with a locking feature of the stem to couple the replacement head to the handle; and wherein a portion of the second component covers the locking element so that no portion of the locking element is exposed at an outer surface of the sleeve portion.

In another embodiment, the invention may be a replacement head for detachable coupling to a handle of an oral care implement, the replacement head comprising: a head portion having a front surface with tooth cleaning elements extending therefrom; a sleeve portion comprising: a body and an elastomeric material overmolded onto the body; a cavity configured to receive a stem of the handle; a proximal edge defining an opening into the cavity; and a locking element configured to mate with a locking feature of the stem to couple the replacement head to the handle; and wherein the locking element comprises a slot formed into the body of the sleeve portion, the elastomeric material forming a surface of the slot.

In still another embodiment, the invention may be a replacement head for detachable coupling to a handle of an oral care implement, the replacement head comprising: a head portion having a front surface with tooth cleaning elements extending therefrom; a sleeve portion comprising a first component formed of a first material and a second component formed of a second material, the first component comprising an inner surface that defines a cavity configured to receive a stem of the handle, a proximal edge of the sleeve portion defining an opening into the cavity; the first component comprising a slot configured to couple the replacement head to the handle, the slot extending entirely through the first component from the outer surface to the inner surface; and wherein the second component forms an annular ring that surrounds a proximal end portion of the first component, a portion of the annular ring forming a surface of the slot.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
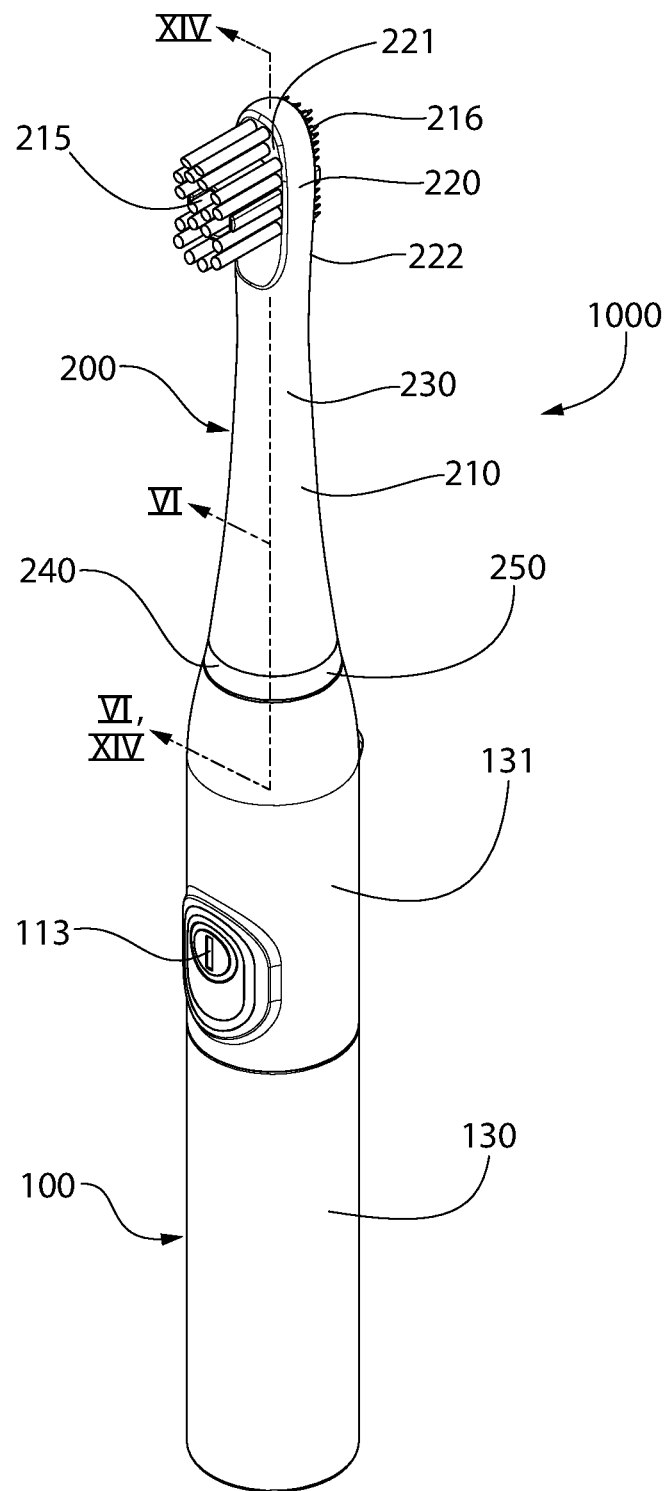
FIG. 1 is a front perspective view of an oral care implement having a replacement head and a handle in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Figure 2:
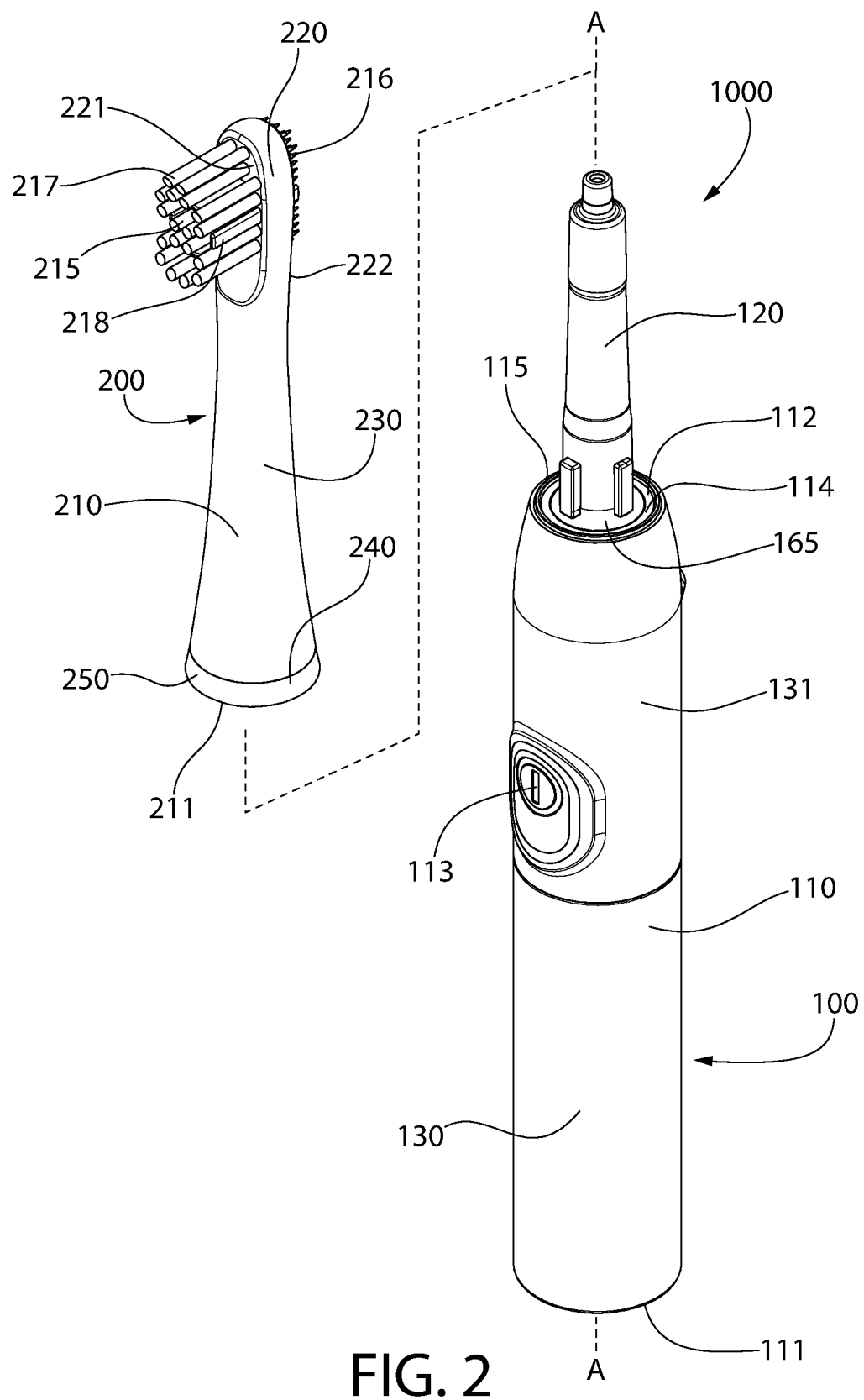
FIG. 2 is a front perspective view of the oral care implement of FIG. 1 illustrating the replacement head detached from a handle.
Figure 3:
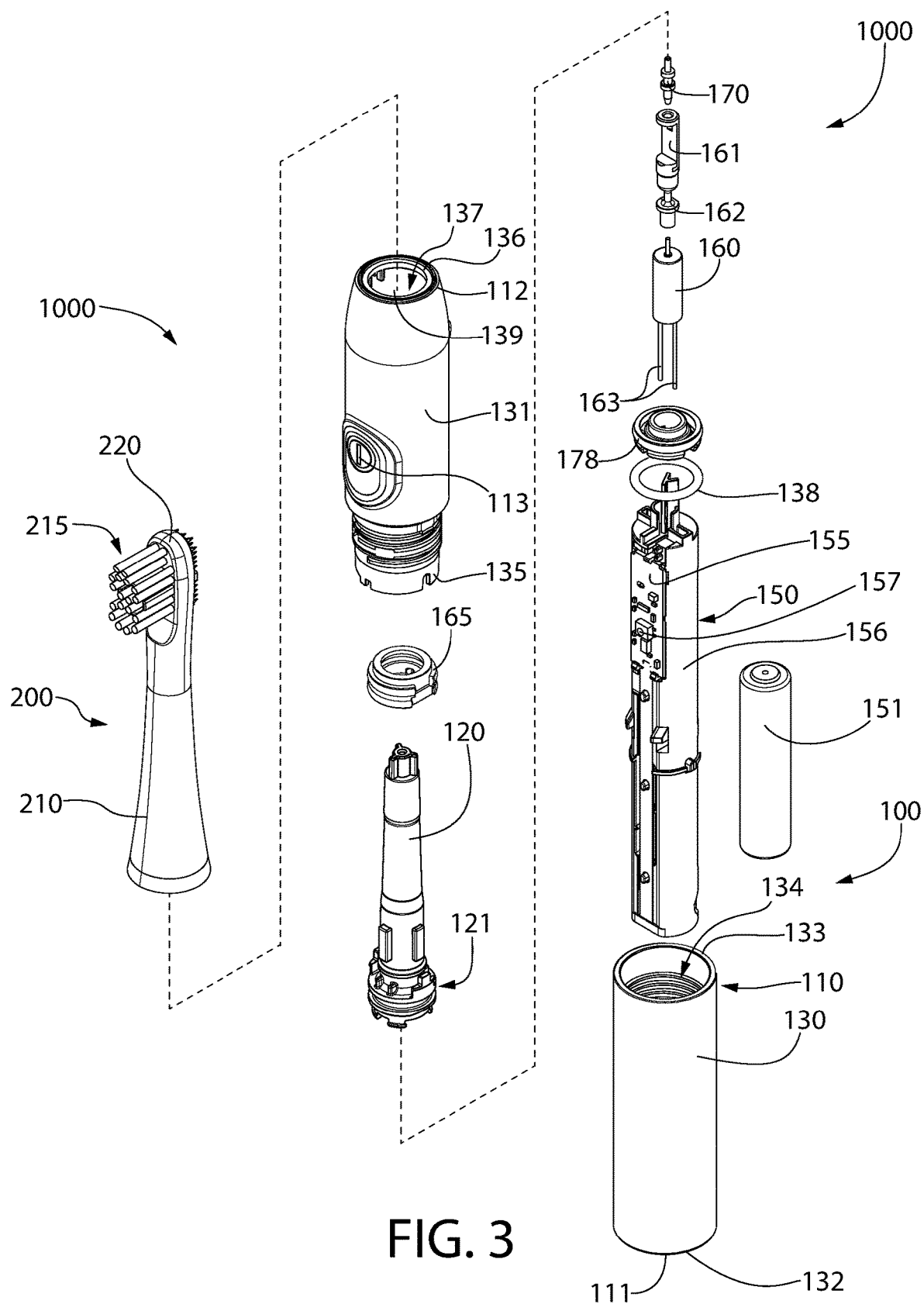
FIG. 3 is an exploded front perspective view of the oral care implement of FIG. 1.
Figure 4:
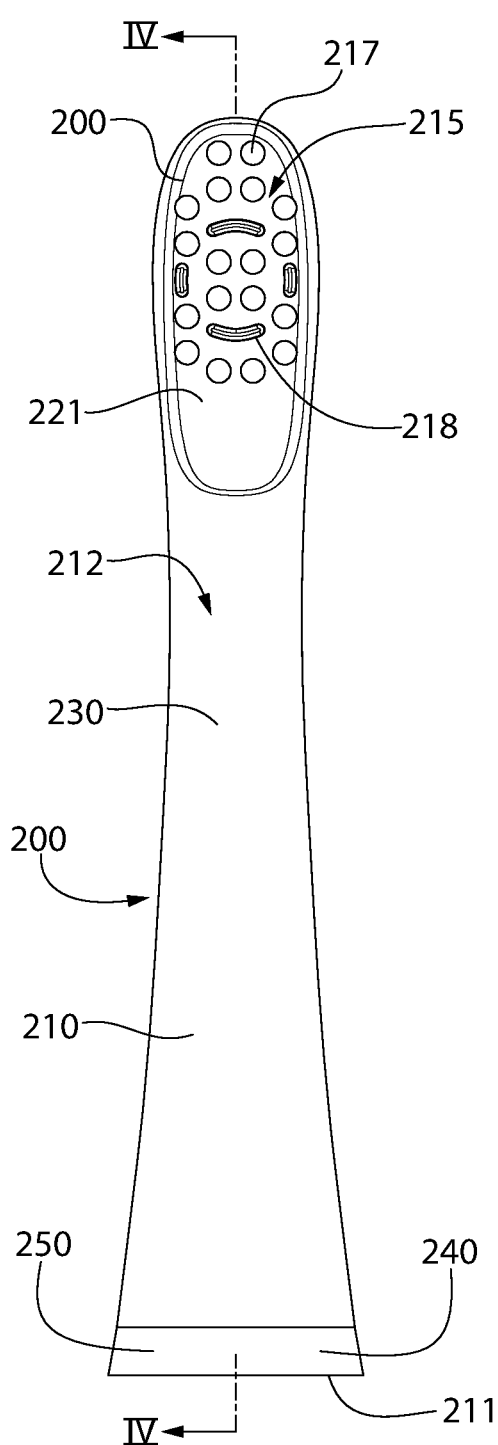
FIG. 4 is a front view of the replacement head of the oral care implement of FIG. 1.

Referring to FIGS. 1-3 concurrently, an oral care implement 1000 is illustrated in accordance with an embodiment of the present invention. The oral care implement 1000 generally comprises a handle 100 and a replacement head 200. The replacement head 200 is detachably coupled to the handle 100. Thus, the replacement head 200 may be repetitively coupled to and detached from the handle 100 as desired. This enables the handle 100 to be kept and reused while the replacement head 200 is replaced with a new replacement head when the cleaning elements of the replacement head 200 become worn.

In the exemplified embodiment, the oral care implement 1000 is a powered or electric toothbrush (including a vibratory element that moves a bristle holder or vibrates the head or portions thereof). Of course, the invention is not to be so limited in all embodiments and in other embodiments the oral care implement 1000 may be a manual toothbrush, a tongue scraper, a gum and soft tissue cleanser, a water pick, an interdental device, a tooth polisher, a specially designed ansate implement having tooth engaging elements, or any other type of implement that is commonly used for oral care.

The handle 100 extends along a longitudinal axis A-A and comprises a gripping portion 110 extending from a proximal end 111 to a distal end 112 and a stem 120 that extends or protrudes from the distal end 112 of the gripping portion 110. In the exemplified embodiment, the stem 120 is not directly attached to the gripping portion 110, but rather it extends through an opening 139 in the distal end 112 of the gripping portion 110. Thus, stating that the stem 120 "extends from" the distal end 112 of the gripping portion 110 does not require a direct coupling between the stem 120 and the distal end 112 of the gripping portion 110, but merely requires that the stem 120 extends in the longitudinal direction A-A beyond the distal end 112 of the gripping portion 110. Of course, the stem 120 may be directly coupled to and extend directly from the distal end 112 of the gripping portion 110 in some embodiments. As discussed below and shown in FIG. 3, in the exemplified embodiment the handle 100 houses all of the electronic components of the oral care implement 1000.

In the exemplified embodiment, the gripping portion 110 of the handle 100 comprises a button 113 on its outer surface that enables a user to power the oral care implement 1000 on and off. Specifically, the button 113, when depressed, engages a switch that powers a motor of the oral care implement 1000 and causes the motor, via its coupling to an eccentric, to create vibrations that enhance a user's cleaning experience. The details of these electronic components will be described more fully herein below.

The replacement head 200 comprises a sleeve portion 210 and a head portion 220. The sleeve portion 210 is the portion that fits over the stem 120 of the handle 100 to couple the replacement head 200 to the handle 100. The head portion 220 has a plurality of tooth cleaning elements 215 extending therefrom for cleaning a user's oral cavity such as the teeth and gums. Additional details of the replacement head 200 will be provided below with reference to FIGS. 1, 2, 4, and 5.

In the exemplified embodiment, the gripping portion 110 of the handle 100 comprises a first part 130 and a second part 131 that are detachably coupled together. Of course, it is possible in other embodiments for the gripping portion 110 to be formed from a single unitary component. However, the two-part gripping portion 110 may make it easier to assemble the various components of the oral care implement 1000 together.

The first part 130 has a closed bottom end 132 and an open top end 133. Of course, in other embodiments the bottom end 132 could be open and a separate end cap could be coupled to the bottom end 132 of the first part 130. Furthermore, the first part 130 comprises a cavity 134 defined by its inner surface. The second part 131 comprises an open bottom end 135, an open top end 136, and a cavity 137 extending between the open bottom and top ends 135, 136. The open top end 136 of the second part 131 of the gripping portion 110 of the handle 100 forms the distal end 112 of the gripping portion 110 and also defines the opening 139 through which the stem 120 extends.

The first part 130 of the gripping portion 110 comprises threads on its inner surface adjacent the open top end 133 and the second part 131 of the gripping portion 110 comprises threads on its outer surface adjacent the open bottom end 135. The first and second parts 130, 131 can therefore be screwed together via engagement between their respective threads. Of course, the invention is not to be so limited and the first and second parts 130, 131 may be configured to be coupled together in other manners, including interference fit, lock and key, boss/detent, hardware (i.e., screws, bolts, etc.), or the like. However, in certain embodiments it is preferred that the first and second parts 130, 131 be capable of being detached from one another for replacement of a battery as described further below. An O-ring 138 (or other type of gasket) may be provided between the first and second parts 130, 131 of the gripping portion 110 to seal the interface of the first and second parts 130, 131 so that water and other fluids cannot pass into the cavities 134, 137 during use of the oral care implement 1000 or otherwise.

An electronics component 150 is housed within the cavities 134, 137 of the first and second parts 130, 131 of the gripping portion 110. Thus, the electronics component 150 may be inserted into the cavity 137 of the second part 131, and then when the first part 130 is coupled to the second part 131, the electronics component 150 is also inserted into the cavity 134 of the first part 130 by extending through the open top end 133 of the first part 130. Specifically, the electronics component 150 has a greater length than the second part 131 of the gripping portion 110 and thus when the electronics component 150 is located within the cavity 137 of the second part 131, a portion of the electronics component 150 extends through the open bottom end 135 of the second part 131. When the first part 130 is later coupled to the second part 131, the portion of the electronics component 150 that extends from the open bottom end 135 of the second part 131 becomes positioned within the cavity 134 of the first part 130.

The electronics component 150 comprises a circuit board 155 comprising the electronic circuitry necessary for proper operation of the oral care implement 1000, including processor(s), memory device(s), switch(es) 157, resistors, capacitors, and the like. The electronics component 150 also comprises a chassis 156 that holds a power source 151, which is shown as a battery exploded away from the electronics component 150 in FIG. 3. Of course, more than one battery may be used. In the exemplified embodiment, the circuit board 155 is coupled to one side of the chassis 156 and the batteries are housed within a compartment located on the opposite side of the chassis 156. Of course, other arrangements are possible in other embodiments. Generally, the electronics component 150 is configured to be coupled to a motor to control operation of the motor such that when the switch 157 is closed the motor is operating and when the switch is open the motor is not operating.

The stem 120 is a separate component from the gripping portion 110. During assembly of the oral care implement 1000, the stem 120 is inserted into the cavity 137 of the second part 131 before the second part 131 is coupled to the first part 130. Specifically, the stem 120 is inserted through the open bottom end 135 of the second part 131 and translated axially within the cavity 137 until a portion of the stem 120 contacts an inner surface of the second part 131 such that the stem 120 can not be translated any further. At this point, a portion of the stem 120 extends from the distal end 112 of the gripping portion 120 as discussed previously. Once the stem 120 is positioned in this manner, the electronics portion 150 is inserted into the cavity 137 of the second part 131 as described above. Finally, after the electronics portion 150 is inserted into the cavity 137 of the second part 131, the first and second parts 130, 131 of the gripping portion 110 may be coupled together to form the handle 100.

Figures 6A, 6B:
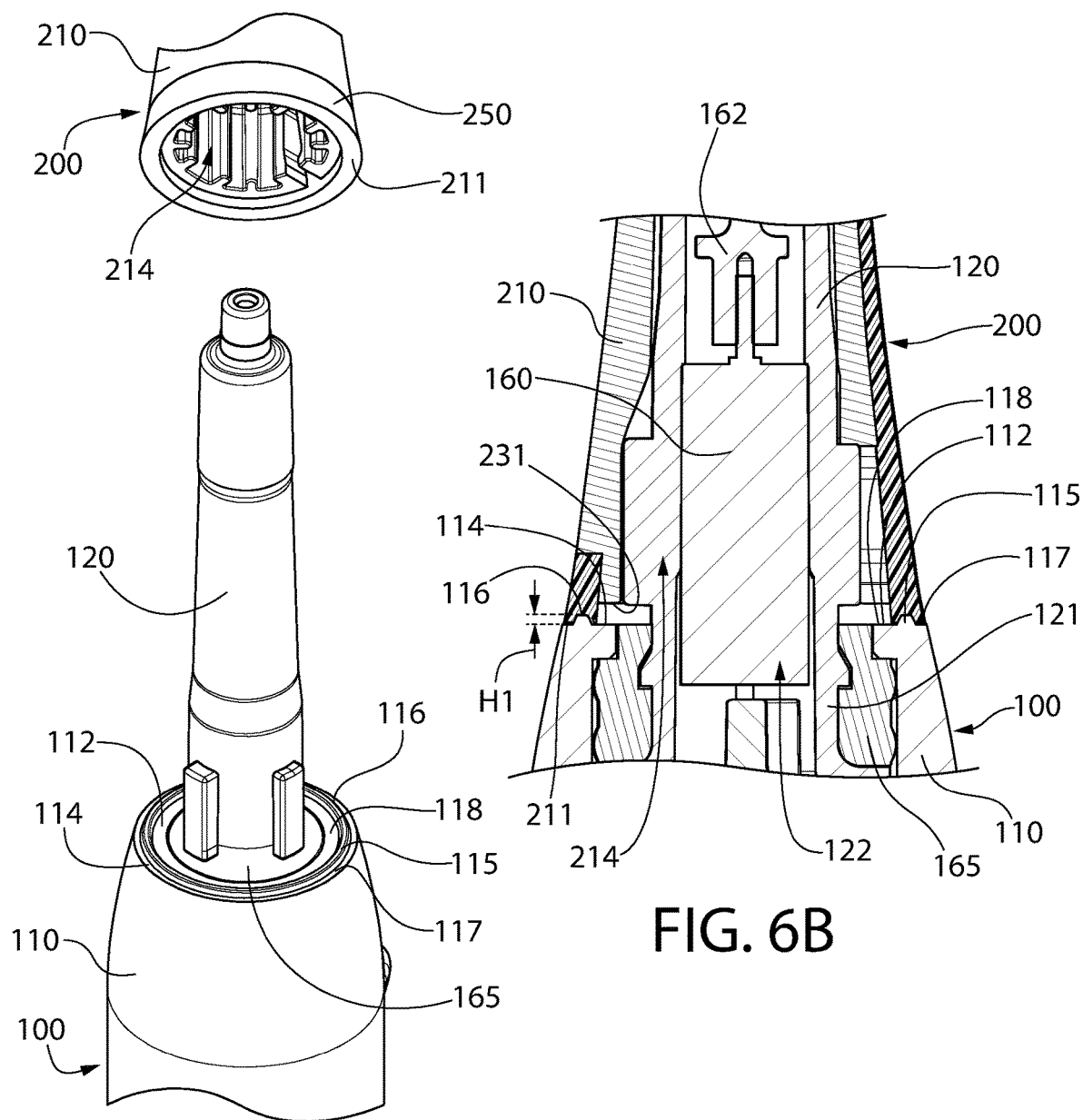
FIG. 6A is a partial view of the oral care implement of FIG. 1 illustrating the refill head aligned with the handle for coupling the refill head to the handle.
FIG. 6B is a cross-sectional view taken along line VI-VI of FIG. 1 in accordance with the oral care implement of FIG. 6A.

A gasket 165 is provided at the junction of the stem 120 and the gripping portion 110 to prevent the ingress of liquids at the location of the junction of those two components. The gasket 165 is coupled to the stem 120 so as to surround a portion of a lower portion 121 of the stem 120. Furthermore, the gasket 165 presses against the inner surface of the second component 131 of the gripping portion 110 to maintain the stem 120 in position without the stem 120 falling into the cavity 137. A portion of the gasket 165 is visible when the handle 100 is fully assembled with the replacement head 200 detached therefrom, as best illustrated in FIG. 2. The interaction of the gasket 165 with the stem 120 and the gripping portion 110 is best shown in FIG. 6B. A second gasket 178 may be coupled to another portion of the lower portion 121 of the stem 120 and collectively the gasket 165 and the second gasket 178 operate to prevent the ingress of fluids into the cavities 134, 137. Of course, one or both of the gasket 165 and the second gasket 178 may be omitted in alternative embodiments.

The stem 120 comprises an inner cavity 122 (FIGS. 6B and 14) that houses a motor 160, an eccentric 161, a coupling member 162 that couples the motor 160 to the eccentric 161, and a guide pin 170. The motor 160, the eccentric 161, and the coupling member 162 may be referred to herein collectively as a vibratory element 199 (labeled in FIGS. 11 and 14) because these components are coupled together and operate collectively to impart vibrations to the head portion 220 and the tooth cleaning elements 215 of the replacement head 200. The motor 160 is electrically coupled to the electronics component 150 and the power source 151 via conductive wires 163 to control operation of the motor 160. When the motor 160 is activated, the eccentric 161 is caused to rotate due to its coupling to the motor 160. Due to the off-center rotation of the eccentric 161 relative to a central axis of the motor, rotation of the eccentric 161 imparts vibrations to the head portion 210 of the replacement head 200. The stem 120, the motor 160, the eccentric 161, the coupling member 162, and the guide pin 170 will be discussed in more detail below with reference to FIGS. 11-14.

Referring to FIGS. 2, 6A, and 6B concurrently, in the exemplified embodiment the distal end 112 of the gripping portion 110 comprises a shoulder 114 that surrounds the stem 120. In the exemplified embodiment, the shoulder 114 is annular or ring shaped. However, the invention is not to be so limited and the shoulder 114 could be square, triangular, pentagonal, hexagonal, or any other shape as may be desired. Thus, the shoulder 114 is not limited to any particular shape. Furthermore, an annular rib 115 protrudes from the shoulder 114. In this embodiment, the annular rib 115 forms a continuous ring-shaped protrusion or wall that extends along the entirety of the shoulder 114 so that the annular rib 115 also surrounds the stem 120. Thus, in this embodiment the annular rib 115 does not have any gaps or spaces therein, but it extends continuously in an annular fashion. However, the annular rib 115 need not be continuous in all embodiments and it may instead form a discontinuous ring-shaped protrusion or wall comprising a plurality of spaced apart rib segments (discussed below with reference to FIGS. 7A and 7B).

Furthermore, although the annular rib 115 is illustrated as being a ring-like protrusion or wall that is circular and smooth, in other embodiments the annular rib 115 may take on other shapes, such as being oval, curvy, sinusoidal, wavy, or the like. For example, the annular rib 115 may have scalloped edges that are rounded, pointed, or anything in between. Thus, although a perfectly smooth circular wall or illustrated in the exemplified embodiment, the invention is not to be so limited in this regard.

The annular rib 115 extends from the shoulder 114 in a central location of the shoulder 114. Of course, the invention is not to be limited by this specific positioning of the annular rib 115 and it may be located along other portions of the shoulder 114. Specifically, in the exemplified embodiment the shoulder 114 comprises a first ring-shaped portion 117 and a second ring-shaped portion 118, the annular rib 115 being located between the first and second ring-shaped portions 117, 118. In the exemplified embodiment, the first ring-shaped portion 117 has a greater diameter than and surrounds the annular rib 115 and the annular rib 115 has a greater diameter than and surrounds the second ring-shaped portion 118. The first and second ring-shaped portions 117, 118 of the shoulder 114 remain exposed despite the existence of the annular rib 115. In the exemplified embodiment, the second ring-shaped portion 118 has a greater width measured in a direction transverse to the longitudinal axis A-A of the handle 100 than the first ring-shaped portion 117. However, in other embodiments the opposite may be true, or the first and second ring-shaped portions 117, 118 of the shoulder 114 may have an identical width.

The annular rib 115 has a height H1 measured from the shoulder 114 to a distal end 116 of the annular rib 115. In the exemplified embodiment, the annular rib 115 extends only minimally from the shoulder 114, and thus the height H1 of the annular rib 115 is about 1 mm or less measured in the direction of the longitudinal axis A-A. Of course, the annular rib 115 may extend a greater height from the shoulder 114 in other embodiments. The annular rib 115 has a constant height H1 and a constant diameter in the exemplified embodiment, although this need not be true in all embodiments. The height H1 and/or diameter of the annular rib 115 could instead be inconstant if so desired. However, having a constant height H1 will make for a better seal between the handle 100 and the replacement head 200 as described herein unless a proximal edge 211 of the replacement head 200 has a similarly inconstant structure.

As best seen in FIG. 6B, in the exemplified embodiment the distal end 116 of the annular rib 115 forms a flat top surface of the annular rib 115, but it may be rounded or the like in other embodiments. Thus, in the exemplified embodiment the annular rib 115 has a cross-sectional shape in the form of a truncated cone, although other shapes are possible without detracting from the benefits that the annular rib 115 provides. In the exemplified embodiment, the annular rib 115 is formed integrally with the gripping portion 110 of the handle 100. Thus, the annular rib 115 is formed of a rigid material, such as hard plastic, along with the remainder of the gripping portion 110 of the handle 100. In other embodiments, an elastomeric material may be provided on the gripping portion 110 to form the shoulder 114 of the gripping portion 110 and the annular rib 115 may be formed integrally with the elastomeric material. Other variations to this will be described below with reference to the embodiments illustrated in FIGS. 7A-10B.

Referring to FIGS. 1, 2, 4, and 5, the replacement head 200 will be described in detail. The replacement head 200 comprises the sleeve portion 210 and the head portion 220 that is coupled to the sleeve portion 210. The sleeve and head portions 210, 220 may be integrally formed as a single unitary structure. The sleeve and head portions 210, 220 may comprise a base or body portion formed of a hard plastic material such as polypropylene or the like and an elastomeric material may be overmolded onto the base or body portion. As mentioned above, the replacement head 200 comprise the plurality of tooth cleaning elements 215 that extend from a front surface 221 of the head portion 220 and a soft tissue cleaner 216 is located on a rear surface 222 of the head portion 220. Of course, the soft tissue cleaner 216 could be omitted in some alternative embodiments.

The tooth cleaning elements 215 are illustrated on the head with a specific arrangement and pattern. Specifically, the tooth cleaning elements 215 include a combination of filament bristles 217 and elastomeric cleaning elements 218 that collectively form a bristle field. In certain embodiments, the exact structure, pattern, orientation, and material of the tooth cleaning elements 215 are not to be limiting of the present invention. Thus, the term "tooth cleaning elements" may be used herein in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof, and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 215 of the present invention can be connected to the head portion 220 in any manner known in the art. For example, staples/anchors, in-mold tufting (IMT) or anchor free tufting (AFT) could be used to mount the cleaning elements/tooth engaging elements. In certain embodiments, the invention can be practiced with various combinations of stapled, IMT or AFT bristles. In the exemplified embodiment, the filament bristles 217 are secured to the head portion 220 using staples/anchors and the elastomeric cleaning elements 218 are integrally formed with the soft tissue cleaner 216 through one or more passageways 219 extending through the head portion 220 from the front surface 221 to the rear surface 222 thereof.

The sleeve portion 210 of the replacement head 200 extends from a proximal edge 211 at a proximal portion of the replacement head 200 to the head portion 220. Furthermore, the sleeve portion 210 of the replacement head 200 comprises an outer surface 212 and an opposite inner surface 213, the inner surface 213 defining a cavity 214. An opening 245 is formed into the sleeve portion 210 at the proximal edge 211 that forms a passageway into the cavity 214. The cavity 214 is sized and shaped to receive the stem 120 of the handle 100 when the replacement head 200 is coupled to the handle 100.

In the exemplified embodiment, the proximal edge 211 of the sleeve portion 210 is formed from or comprises an elastomeric material. More specifically, the replacement head 200 comprises a first component 230 formed of a first material and a second component 240 formed of a second material. In the exemplified embodiment, the first component 230 comprises a rigid material such as a hard plastic material (i.e., polypropylene or the like) and forms a main body of the replacement head 200 and the second component 240 comprises a resilient material such as a thermoplastic elastomer or other elastomeric material. The second material 240 may be injection molded onto the first material 230 to form the replacement head 200.

The first component 230 extends from a bottom edge 231 to a top end 232 and comprises a bottom portion 233 that includes the bottom edge 231. In the exemplified embodiment, the second material 240 is an integral mass of elastomeric material comprising a first portion that forms an annular ring 250 at the proximal portion of the sleeve portion 210, a second portion that forms the soft tissue cleaner 216 on the rear surface 222 of the head portion 220, a third portion 236 that extends between the annular ring 250 and the soft tissue cleaner 216, and a fourth portion that forms the elastomeric cleaning elements 218 extending from the front surface 221 of the head portion 220. A first portion 251 of the annular ring 250 surrounds the bottom portion 233 of the first component 230 and a second portion 252 of the annular ring 250 extends beyond the bottom edge 231 of the first component 230. Because the second portion 252 of the annular ring 250 extends beyond the bottom edge 231 of the first component 230, the second portion 252 of the annular ring 250 is not positioned in an abutting relationship with any part of the first component 230. Thus, the second portion 252 of the annular ring 250 forms a cantilever. Due to this and the resiliency of the material of the second component 240, the second portion 252 of the annular ring 250 has a significant amount of flexibility in radial and axial directions. It should be noted that the annular ring 250 does not at all cover the bottom edge 231 of the first component 230, and thus the bottom edge 231 of the first component 230 remains exposed when viewed from the bottom of the replacement head 200.

In the exemplified embodiment, the first component 230 comprises an annular recess 234 within the bottom portion 233 and the first portion 251 of the annular ring 250 is located within the annular recess 234. As a result, an outer surface 253 of the annular ring 250 is flush with an outer surface 235 of the first component 230 at the interface of the first component 230 and the annular ring 250 of the second component 240. Furthermore, it should be appreciated that the entirety of the inner surface 213 of the sleeve portion 210 of the replacement head 200 is formed by the first component 230. Thus, no portion of the second component 240 forms the inner surface 213 of the sleeve portion 210 or covers any portion of the inner surface of the first component 230. The second component 240 is only positioned atop of (i.e., overmolded onto) parts of the outer surface of the first component 230.

Due to the structure outlined above, when the replacement head 200 is viewed by a consumer, the annular ring 250 on the proximal portion of the sleeve portion 210 will stand out in a visual sense. In some embodiments, this may be made more prominent by forming the first component 230 out of a hard plastic material having a first color and forming the second component 240 out of an elastomeric material having a second color that is different than the first color. The elastomeric annular ring 250 at the bottom of the sleeve portion 210 provides both an aesthetic benefit as well as a functional one, described more fully below.

Referring to FIGS. 6A and 6B concurrently, the proximal edge 211 of the sleeve portion 210, which is formed from an elastomeric material in the exemplified embodiment, forms a generally flat surface in that it is free of any depressions therein or protrusions extending therefrom. The proximal edge 211 is perpendicular to the longitudinal axis A-A in the exemplified embodiment, but it could be oblique to the longitudinal axis A-A in other embodiments.

When the replacement head 200 is coupled to the handle 100, the stem 120 of the handle 100 is located within the cavity 214 of the sleeve portion 210 of the replacement head 200. Furthermore, the proximal edge 211 of the sleeve portion 210 is located adjacent to the shoulder 114 of the gripping portion 110. As discussed above, the annular rib 115 protrudes from the shoulder 114 and the proximal edge 211 of the sleeve portion 210 comprises an elastomeric material. As a result, when the replacement head 200 is coupled to the handle 100, the annular rib 115 contacts, and potentially deforms, the elastomeric or resilient material of the proximal edge 211 of the sleeve portion 210. This creates a tight seal between the proximal edge 211 of the sleeve portion 210 of the replacement head 200 and the shoulder 114 of the gripping portion 110 of the handle 100 that prevents fluids such as toothpaste, water, saliva, and/or slurry from flowing into the area between the sleeve portion 210 of the replacement head 200 and the stem 120 of the handle 100. This is beneficial because users rarely detach the replacement head 200 from the handle 100 until it is being exchanged for a new replacement head 200, and thus fluid in the cavity 214 of the replacement head 200 may turn to bacteria over time. The seal between the proximal edge 211 of the replacement head 200 and the annular rib 115 also provides an additional barrier against fluid flow into the interior of the gripping portion 110, which houses the electronics component 150 as mentioned above.

Figures 7A, 7B:
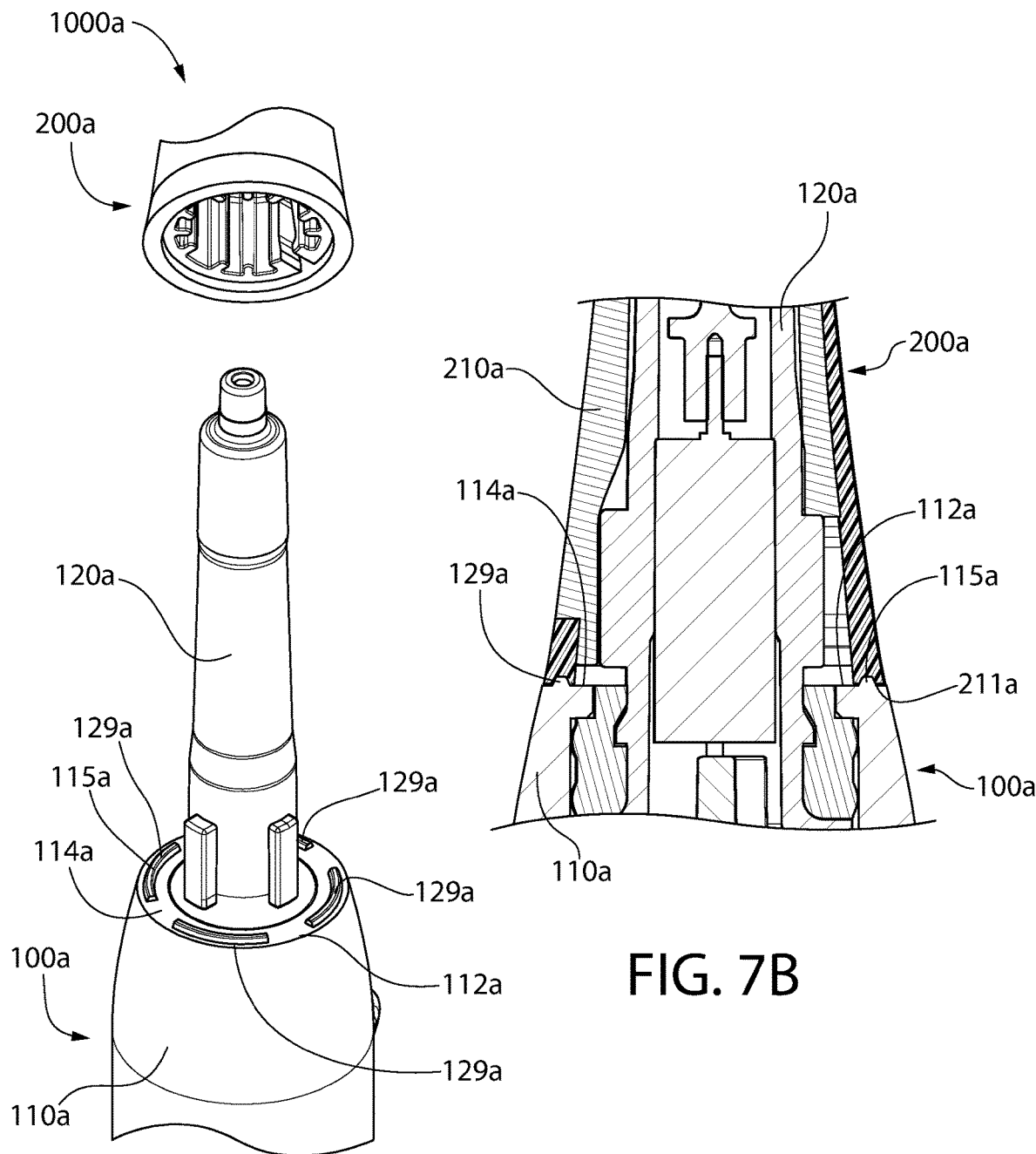
FIG. 7A is a partial view of a first alternative embodiment of an oral care implement illustrating the refill head aligned with the handle for coupling the refill head to the handle.
FIG. 7B is a cross-sectional view taken along line VI-VI of FIG. 1 in accordance with the first alternative embodiment of the oral care implement of FIG. 7A.

Referring to FIGS. 7A and 7B, an alternative embodiment of an oral care implement 1000a will be described. The oral care implement 1000a comprises a handle 100a and a replacement head 200a. The replacement head 200a is identical to the replacement head 200 of FIGS. 1-6B and thus it will not be further described herein, it being understood that the description above is applicable. The handle 100a is identical to the handle 100 of FIGS. 1-6B with the exception of the description below. Thus, the description of the handle 100 above is applicable to the handle 100a with the exception of that which is described below with specific reference to the handle 100a.

The handle 100a comprises a gripping portion 110a and a stem 120a protruding from a distal end 112a of the gripping portion 110a. The distal end 112a of the gripping portion 110a forms a shoulder 114a that circumferentially surrounds the stem 120a. Furthermore, the gripping portion 110a comprises an annular rib 115a protruding from the shoulder 114a. In this embodiment, the annular rib 115a is identical to the annular rib 115 except that it is not a continuous ring-like protrusion or wall. Rather, in this embodiment the annular rib 115a forms a discontinuous ring-like protrusion or wall comprising a plurality of spaced apart rib segments 129a each of which protrudes form the shoulder 114a. Specifically, each of the rib segments 129a is circumferentially spaced apart from the rib segments 129a that are adjacent to it. As seen in FIG. 7B, when the replacement head 200a is coupled to the handle 100a, the rib segments 129a of the annular rib 115a contact and potentially deform the resilient material at a proximal edge 211a of a sleeve portion 210a of the replacement head 100a.

Figures 8A, 8B:
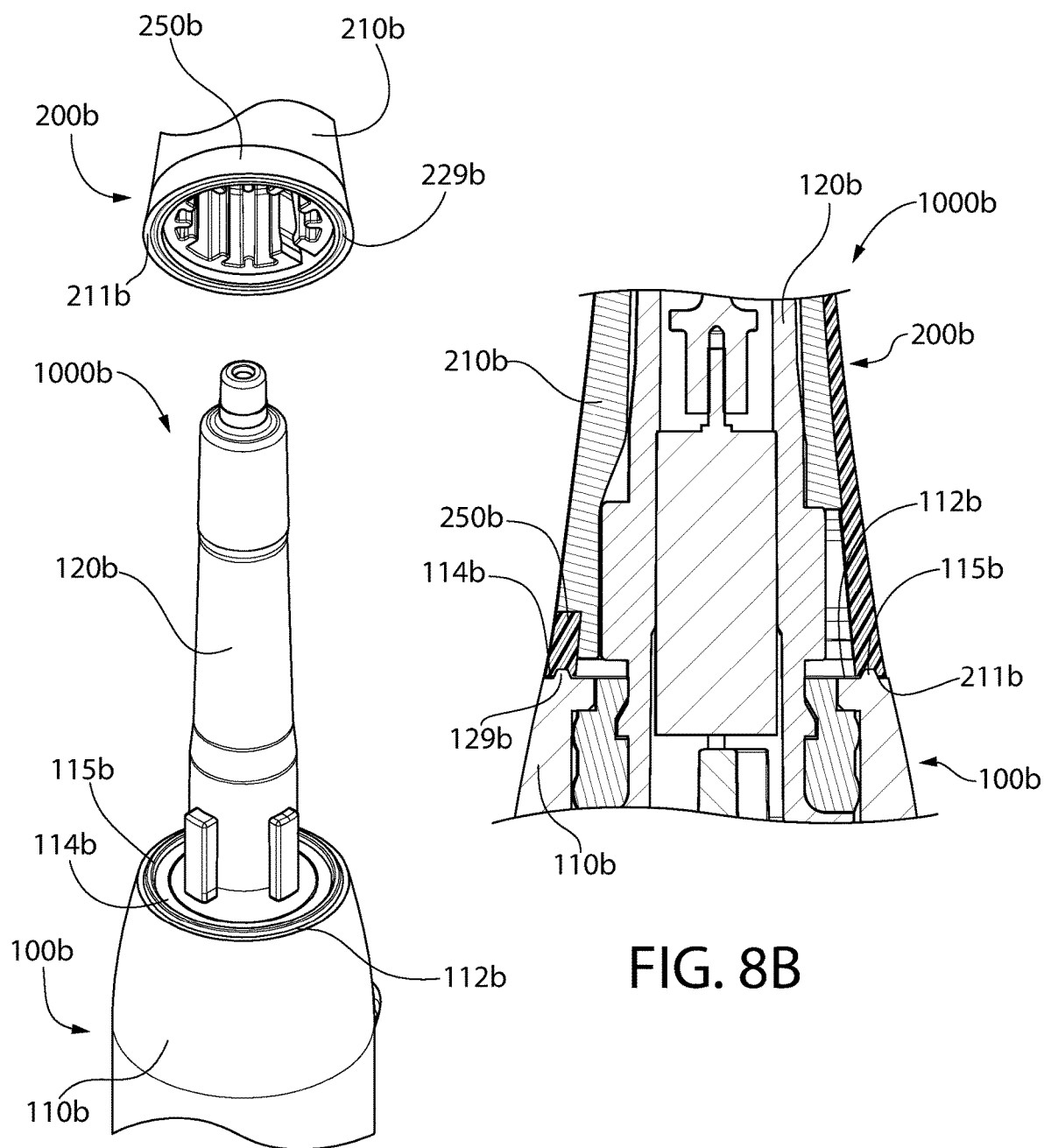
FIG. 8A is a partial view of a second alternative embodiment of an oral care implement illustrating the refill head aligned with the handle for coupling the refill head to the handle.
FIG. 8B is a cross-sectional view taken along line VI-VI of FIG. 1 in accordance with the second alternative embodiment of the oral care implement of FIG. 8A.

Referring to FIGS. 8A and 8B, another alternative embodiment of an oral care implement 1000b will be described. The oral care implement 1000b generally comprises a handle 100b and a replacement head 200b that is detachably coupled to the handle 100b. In this embodiment, the handle 100b is identical to the handle 100 of FIGS. 1-6B and thus it will not be described in any detail herein, it being understood that the description of the handle 100 is applicable. Furthermore, the replacement head 200b is quite similar to the replacement head 200 of FIGS. 1-6B and thus except for the differences noted herein below, the description of the replacement head 200 is applicable.

The replacement head 200b comprises a sleeve portion 210b having a proximal edge 211b that is formed of a resilient or elastomeric material such as a thermoplastic elastomer. The sleeve portion 210b may have an annular ring 250b formed of elastomeric material as with the embodiment of FIGS. 1-6B. The difference between the replacement head 200b and the replacement head 200 is that the replacement head 200b comprises an annular depression 229b formed into the proximal edge 211b of the sleeve portion 210b. Thus, in the exemplified embodiment the annular depression 229b is formed into the elastomeric material that forms the proximal edge 211b of the sleeve portion 210b of the replacement head 200b. However, in other embodiments the proximal edge 211b of the sleeve portion 210b may be formed of a hard plastic rather than a resilient material while still having the annular depression 229b formed therein.

As seen in FIG. 8B, when the replacement head 200b is coupled to the handle 100b, the annular rib 115b protruding from the shoulder 114b at the distal end 112b of the gripping portion 110b of the handle 100b nests within the annular depression 229b formed into the proximal edge 211b of the sleeve portion 210b of the replacement head 200b. Thus, due to the incorporation of the annular depression 229b into the proximal edge 211b of the sleeve portion 210b, the annular rib 115b does not deform the resilient material at the proximal edge 211b of the sleeve portion 210b. Rather, the annular rib 115b simply nests within the annular depression 229b, thereby forming a tight seal to prevent the flow of fluid (saliva, toothpaste slurry, etc.) past the interface of the replacement head 200b and the handle 100b. Furthermore, because the proximal edge 211b of the sleeve portion 210b does not need to be deformed to accommodate the annular rib 115b, as noted above it is possible in this embodiment to form the proximal edge 211b of the sleeve portion 210b out of a rigid material such as a hard plastic rather than forming it out of a resilient material such as a thermoplastic elastomer.

Figures 9A, 9B:
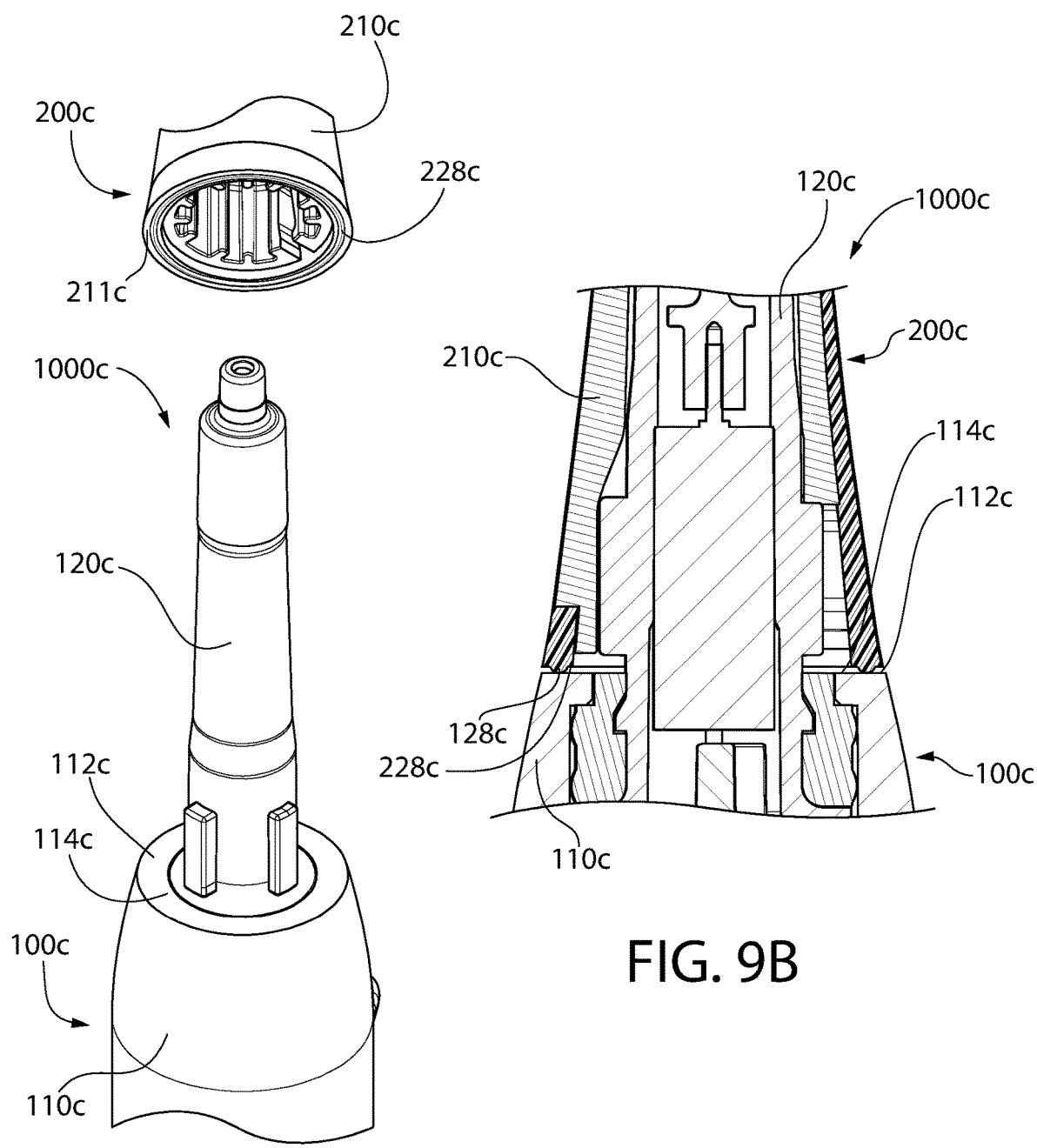
FIG. 9A is a partial view of a third alternative embodiment of an oral care implement illustrating the refill head aligned with the handle for coupling the refill head to the handle.
FIG. 9B is a cross-sectional view taken along line VI-VI of FIG. 1 in accordance with the third alternative embodiment of the oral care implement of FIG. 9A.

Referring to FIGS. 9A and 9B, yet another alternative embodiment of an oral care implement 1000c is illustrated. The oral care implement 1000c generally comprises a handle 100c and a replacement head 200c. In this embodiment, the handle 100c is identical to the handle 100 of FIGS. 1-6B except that the annular rib 115 has been removed. Thus, the handle 100c comprises a gripping portion 110c and a stem 120c protruding from a distal end 112c of the gripping portion 110c. The distal end 112c of the gripping portion 110c forms a shoulder 114c that circumferentially surrounds the stem 120c. However, in this embodiment the shoulder 114c forms a smooth, flat surface and there is no rib protruding therefrom.

The replacement head 200c comprises a sleeve portion 210c having a proximal edge 211c. In this embodiment, the proximal edge 211c of the sleeve portion 210c is formed from a resilient or elastomeric material. However, the proximal edge 211c of the sleeve portion 210c need not be formed from an elastomeric material in all embodiments and it could be formed from a rigid material (i.e., hard plastic such as polypropylene or the like) in other embodiments. Furthermore, in this embodiment an annular rib 228c protrudes from the proximal edge 211c of the sleeve portion 210c. Thus, the main difference between this embodiment and those previously described is that the annular rib 228c protrudes from the proximal edge 211c of the sleeve portion 210c rather than from the shoulder 114c of the gripping portion 110c of the handle 100c. The annular rib 228c may form a continuous ring-like protrusion or wall or may form a discontinuous ring-like protrusion or wall comprising spaced apart rib segments as described above with regard to the previously disclosed embodiments.

As shown in FIG. 9B, when the replacement head 200c is coupled to the handle 100c, the annular rib 228c of the replacement head 200c contacts the shoulder 114c of the gripping portion 110c of the handle 100c. In embodiments whereby the annular rib 228c is formed from an elastomeric material, the annular rib 228c may be deformed as it contacts the shoulder 114c, thereby creating a leak-tight seal between the replacement head 100c and the handle 200c. Of course, the annular rib 228c may alternatively be formed from a rigid plastic material.

Figures 10A, 10B:
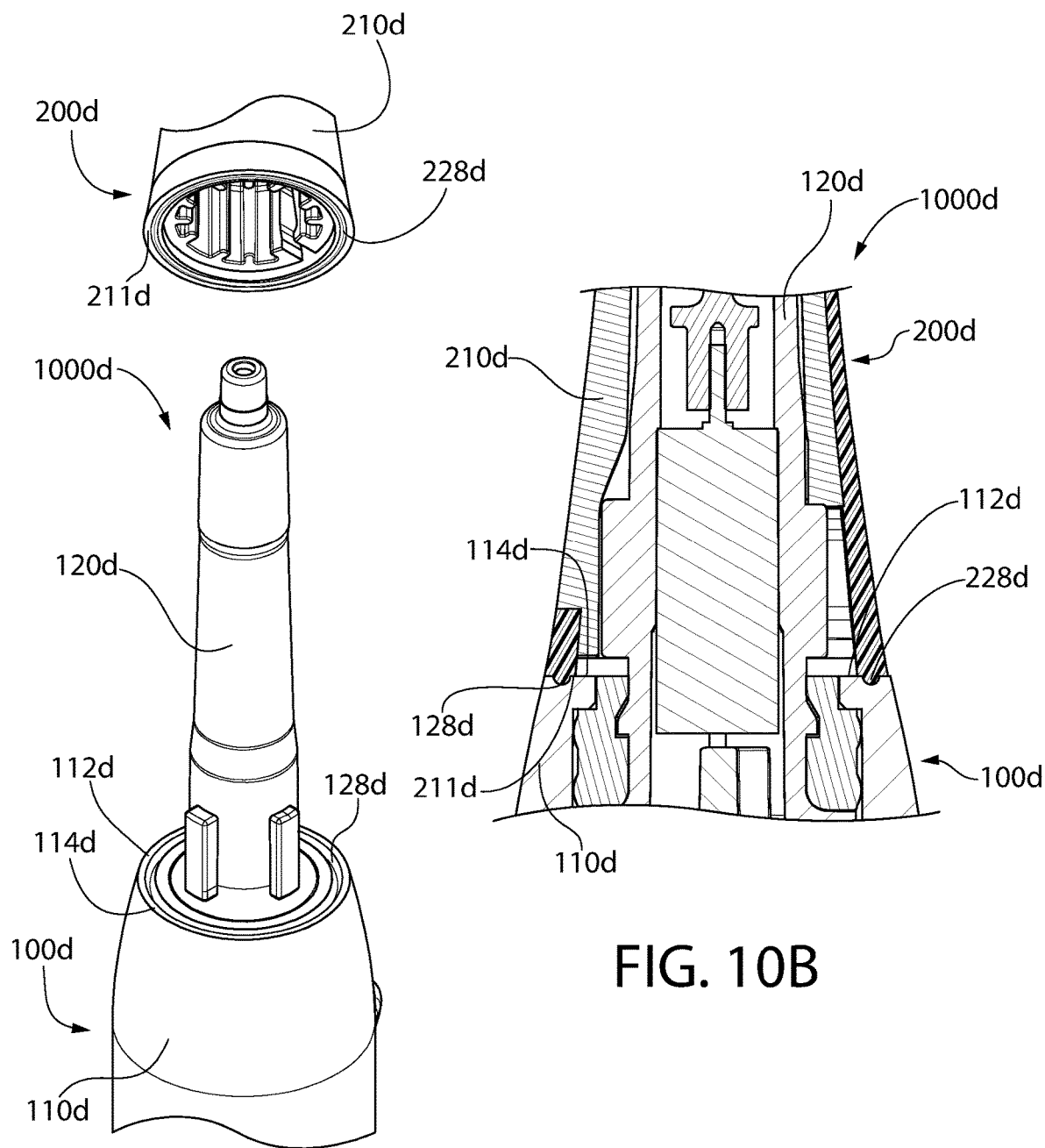
FIG. 10A is a partial view of a fourth alternative embodiment of an oral care implement illustrating the refill head aligned with the handle for coupling the refill head to the handle.
FIG. 10B is a cross-sectional view taken along line VI-VI of FIG. 1 in accordance with the fourth embodiment of the oral care implement of FIG. 10A.

Referring to FIGS. 10A and 10B, a final alternative oral care implement 1000d is illustrated. The oral care implement 1000d comprises a handle 100d and a replacement head 200d. The handle 100d comprises a gripping portion 110d and a stem 120d protruding from a distal end 112d/shoulder 114d of the gripping portion 110d. The replacement head 200d comprises a sleeve portion 210d having a proximal edge 211d. The replacement head 200d is identical to the replacement head 200d in that it comprises an annular rib 228d protruding from the proximal edge 211d of the sleeve portion 210d. In this embodiment, the proximal edge 211d comprises or is formed from a resilient/elastomeric material, although it is not required in all embodiments and it could be formed from a hard plastic material in other embodiments.

The main difference between the oral care implement 1000d and the oral care implement 100c is that an annular depression 128d is formed into the shoulder 114d at the distal end 112d of the gripping portion 110d. As a result, when the replacement head 200d is coupled to the handle 100d, the annular rib 228d protruding from the proximal edge 211d of the sleeve portion 210d nests within the annular depression 128d formed into the shoulder 114d of the gripping portion 110d. Thus, regardless of whether the annular rib 228d is formed from a resilient material (such as thermoplastic elastomer) or a rigid material (such as hard plastic), a tight seal will be formed between the replacement head 200d and the handle 100d as the annular rib 228d nests within the annular depression 128d.

In each of these embodiments of the oral care implements 1000a-d, the annular rib protruding from one of the proximal edge 211a-d of the tubular sleeve 210a-d of the replacement head 200a-d or from the shoulder 114a-d of the gripping portion 110a-d of the handle 100a-d interacts with the other one of the proximal edge 211a-d and the shoulder 114a-d to create a seal that prevents fluids such as toothpaste, water, saliva, and slurry from reaching the internal stem of the oral care implement 1000a-d. This eases the cleaning and maintenance routine for the user of the oral care implement 1000a-d. This is true regardless of whether the annular rib protrudes from the replacement head 200a-d or from the handle 100a-d and regardless of whether the annular rib engages a flat surface of the replacement head 200a-d or handle 100a-d or whether the annular rib nests within a depression in the replacement head 200a-d or handle 100a-d. In some embodiments, at least one of the interface surfaces (i.e., the proximal edge 211a-d of the replacement head 200a-d and the shoulder 114a-d of the gripping portion 110a-d of the handle 100a-d) comprises a resilient material. Either the same interface surface that comprises the resilient material or the other interface surface comprises the annular rib. Thus, there is plenty of variation in structure possible while still achieving the function of preventing fluid from leaking into the interior of the various components of the oral care implements 1000a-d.

Referring to FIGS. 11-14, the stem 120 of the oral care implement 1000 of FIGS. 1-6B and the components that are housed within the inner cavity 122 of the stem 120 will be described in more detail. The stem 120 comprises an inner surface 123 and an opposite outer surface 124. The inner cavity 122 of the stem 120 is defined by the inner surface 123 of the stem 120 and an upper wall 125 of the stem 120. As described previously, the motor 160, the eccentric 161, the coupling member 162, and the guide pin 170 are at least partially housed or contained within the inner cavity 122 of the stem 120. Furthermore, the motor 160 is coupled to the electronics component 150 that is located within the handle 110 via wires 163 so that the power source of the electronics component 150 can provide power to the motor 160 when it is desired to activate the motor 160.

Figure 11:
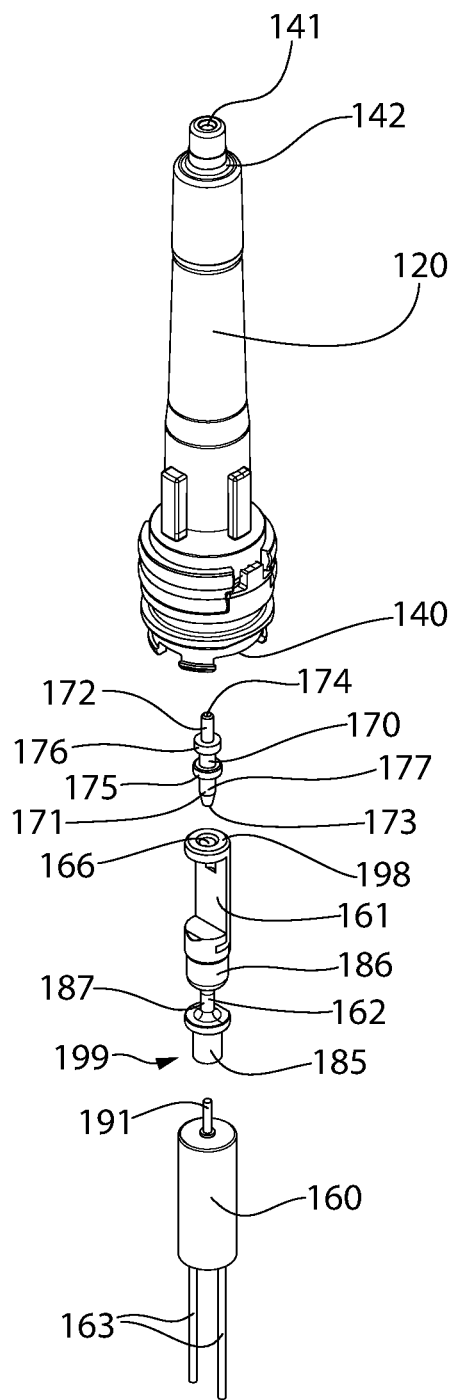
FIG. 11 is an exploded view of a stem of the handle of the oral care implement of FIG. 1.
Figure 12:
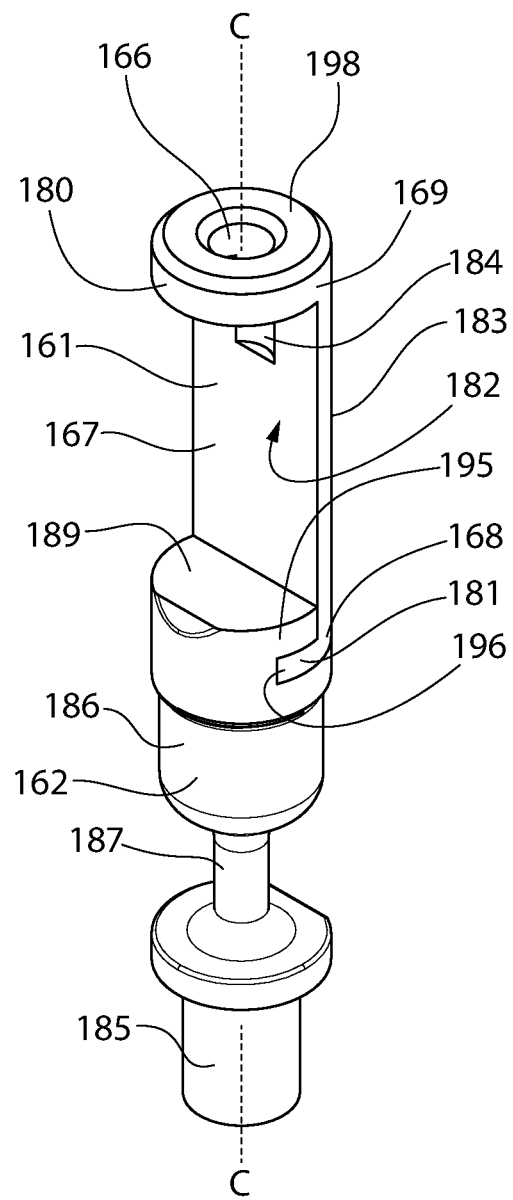
FIG. 12 is a top front perspective view of an eccentric and a coupling member of the oral care implement of FIG. 1.
Figure 13:
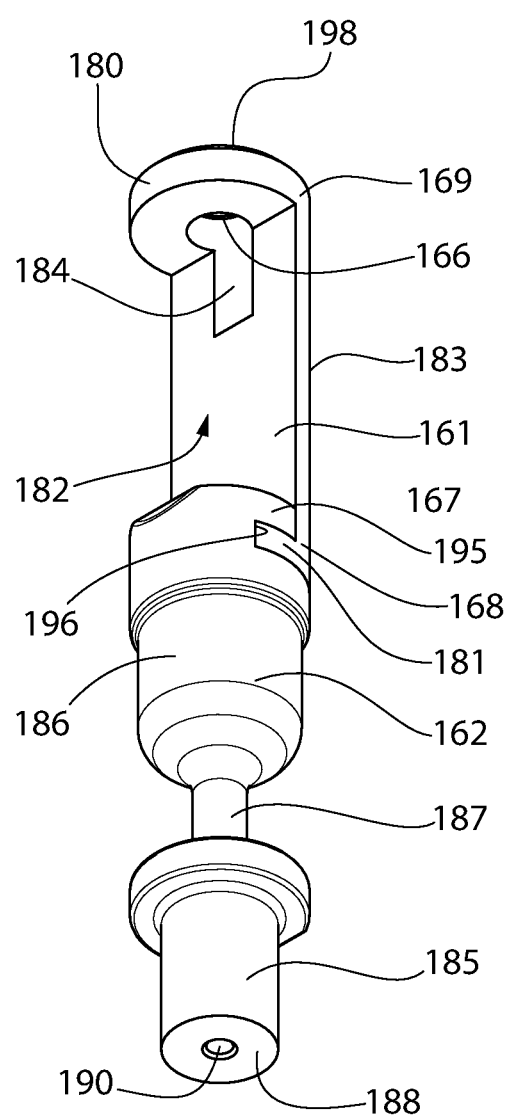
FIG. 13 is a bottom front perspective view of the eccentric and the coupling member of FIG. 12.
Figure 14:
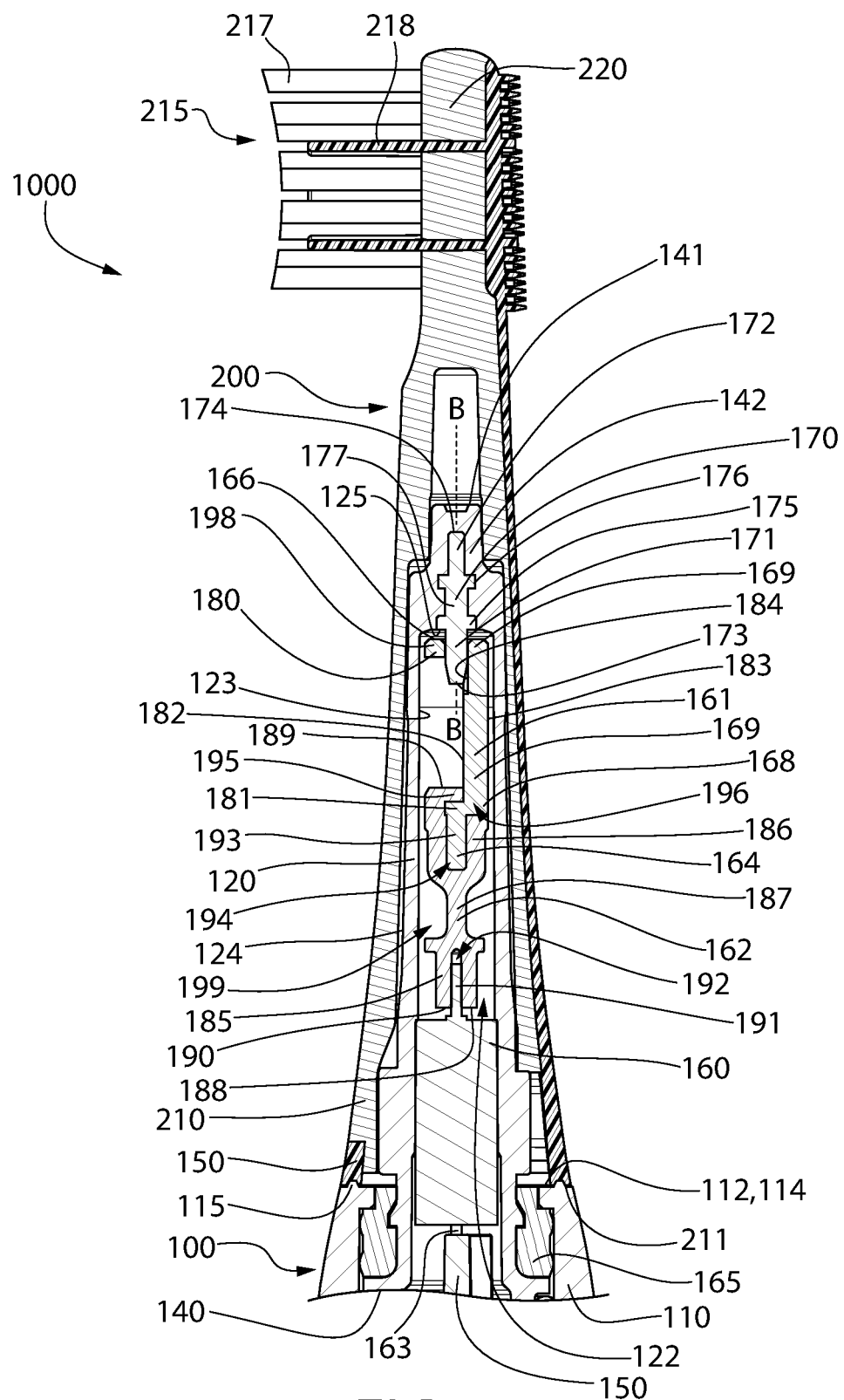
FIG. 14 is a cross-sectional view taken along line XIV-XIV of FIG. 1.

Referring specifically, to FIGS. 11 and 14, the guide pin 170 comprises a first portion 171 and a second portion 172. The second portion 172 of the guide pin 170 is embedded within the stem 120 while the first portion 171 of the guide pin 170 protrudes from the upper wall 125 of the stem 120 into the inner cavity 122 of the stem 120. Thus, the guide pin 170 is fixedly coupled to the stem 120 due to the second portion 172 of the guide pin 170 being embedded within the stem 120. As a result of this fixed coupling of the guide pin 170 to the stem 120, the guide pin 170 is non-rotatable and non-movable relative to the stem 120. Stated another way, the guide pin 170 is axially and rotationally fixed relative to the stem 120 such that the guide pin 170 is non-movable relative to the stem 120.

To be even more specific, the stem 120 is preferably formed of a rigid material, such as a hard plastic like polypropylene or the like. The stem 120 extends from a proximal end 140 to a distal end 141. The stem 120 comprises an upper portion 142 located between the upper wall 125 of the stem 120 and the distal end 141 of the stem 120. The second portion 172 of the guide pin 170 is embedded within the upper portion 142 of the stem 120. Thus, the rigid material of the stem 120 completely surrounds the second portion 172 of the guide pin 170 to affix the guide pin 170 to the stem 120. The first portion 171 of the guide pin 170 extends from the upper wall 125 of the stem 120 into the inner cavity 122 of the stem 120 so that the first portion 171 of the guide pin 170 is suspended within the inner cavity 122 of the stem 120 in a cantilevered manner.

The guide pin 170 is elongated along an axis B-B from a first end 173 to a second end 174. The first portion 171 of the guide pin 170 comprises the first end 173 and the second portion 172 of the guide pin 170 comprises the second end 174. In the exemplified embodiment, the guide pin 170 comprises a main body 177, a first ring-like protrusion 175, and a second ring-like protrusion 176. Each of the first and second ring-like protrusions 175, 176 extend from the main body 177 of the guide pin 170 along the second portion 172 of the guide pin 170 in a radial manner. Thus, in the exemplified embodiment each of the first and second ring-like protrusions 175, 176 circumferentially surround a portion of the main body 177 of the guide pin 170 within the second portion 172 of the guide pin 170. Although in the exemplified embodiment the first and second ring-like protrusions are ring-like in shape, the invention is not to be so limited and they could merely be one or more linear elements that protrude transversely from the main body 177. The first and second ring-like protrusions 175, 176 assist in maintaining the guide pin 170 fixed to the stem 120 as described herein. Thus, any shaped feature, whether it be annular, linear, or the like, can be used so long as it enhances the affixation of the guide pin 170 to the stem 120. Although two of the ring-like protrusions are illustrated in the exemplified embodiment, a single ring-like protrusion or more than two ring-like protrusions might be used in other embodiments without detracting from the functionality of those features.

The first and second ring-like protrusions 175, 176 are axially spaced apart from one another along the second portion 172 of the guide pin 170. When the guide pin 170 is fixed to the stem 120 as described herein, a portion of the material of the stem 120, which is preferably a rigid material, is located between the first and second ring-like protrusions 175, 176. This serves to make it extremely difficult to remove the guide pin 170 from its attachment to the stem 120. Specifically, pulling on the guide pin 170 relative to the stem 120 in the axial direction of the guide pin 170 will not easily result in separating the guide pin 170 from the stem 120 due to the interaction between at least the second ring-like protrusion 176 and the rigid material of the stem 120. In fact, in certain embodiments it would be impossible to remove the guide pin 170 from the stem 120 without breaking the stem 120. If the guide pin 170 were simply an elongated member without the ring-like protrusions, it might be possible to pull on the guide pin 170 in the axial direction with sufficient force to remove the second portion 172 of the guide pin 170 from the upper portion 142 of the stem 140. The ring-like protrusions 175, 176 make this type of action difficult if not impossible. In the exemplified embodiment, the guide pin 170 is formed out of a metal material, although the invention is not to be so limited and other rigid materials including hard plastics or the like could be used for the guide pin 170.

Referring again to FIGS. 11-14 concurrently, the eccentric 161 and the coupling member 162 will be described in greater detail. The eccentric 161 comprises a first end 164 that is operably coupled to the motor 160 (indirectly via the coupling member 162 in the exemplified embodiment but this could be a direct coupling in other embodiments) and a second end 198 that is coupled to the guide pin 170. Specifically, the second end 198 of the eccentric 161 comprises an aperture 166 that receives the first portion 171 of the guide pin 170 when the eccentric 161 is properly housed within the inner cavity 122 of the stem 120.

To be more specific, the eccentric 161 comprises a main body 167 extending along a longitudinal axis C-C from a first end 168 to a second end 169. Furthermore, the eccentric 161 comprises a first flange 180 extending transversely from the second end 169 of the main body 167 and a second flange 181 extending transversely from the first end 168 of the main body 167. The main body 167 of the eccentric 161 comprises an inner surface 182 and an opposite outer surface 183. In the exemplified embodiment, the inner surface 182 is flat/planar and the outer surface 183 is convex. However, in other embodiments the inner surface 182 could be concave or convex and the outer surface 183 could be flat or concave and thus this particular feature is not necessarily limiting of the present invention. Each of the first and second flanges 180, 181 extends from the inner surface 182 of the main body 167. The first flange 180 forms the second end 198 of the eccentric 161 and thus in the exemplified embodiment the aperture 166 is formed into the first flange 180.

Furthermore, the main body 167 of the eccentric 161 comprises a depression 184 formed into the inner surface 182. In the exemplified embodiment, the depression 184 is elongated in a direction of the longitudinal axis C-C. The depression 184 extends from the second end 169 of the main body 167 towards the first end 168 of the main body 167 along a portion of the length of the main body 167. In the exemplified embodiment, the main body 167 has a length measured between the first and second ends 168, 169 and the depression 184 extends along the mean body 167 for a distance that is less than one-half, or less than one-third, of the length of the main body 167. The depression 184 could have a length greater than that which is shown in the exemplified embodiment in alternative embodiments without detracting from the functionality of the invention described herein.

Referring to FIG. 14, as noted above the guide pin 170 is fixed within the upper portion 142 of the stem 120 with the first portion 171 of the guide pin 170 extending from the upper wall 125 of the stem 120 and into the inner cavity 120 of the stem 120. When the eccentric 161 is translated into the inner cavity 122 of the stem 120, the first portion 171 of the guide pin 170 enters into and through the aperture 166 in the eccentric 161. Furthermore, the first portion 171 of the guide pin 170 nests within the depression 184 in the inner surface 182 of the main body 167 of the eccentric 161. Thus, the guide pin 170 serves as a structure that maintains the eccentric 161 in a desired position within the inner cavity 122 of the stem 120 even as the eccentric 161 rotates due to its operable coupling to the motor 160. As the eccentric 161 rotates during use of the oral care implement 1000, the first portion 171 of the guide pin 170 remains located within the aperture 166 and nested within the depression 184. Thus, it could be said that the eccentric 161 rotates around the first portion 171 of the guide pin 170 during operation. The guide pin 170 prevents excessive rattling of the eccentric 161 within the inner cavity 122 of the stem 120 which could otherwise result in an uncomfortable amount of vibration to the head portion 220 during use of the oral care implement 1000.

Referring again to FIGS. 11-14 concurrently, the coupling member 162 will be described along with its manner of attachment to the motor 160 and the eccentric 161. In certain embodiments, the eccentric 161 may be formed of metal and the coupling member 162 may be formed of plastic. However, other materials are possible for the coupling member 162 and the eccentric 161 in alternative embodiments. The coupling member 162 comprises a first portion 185 that is coupled to the motor 160, a second portion 186 that is coupled to the second flange 181 of the eccentric 161, and a central portion 187 located between the first and second portions 185, 186. Thus, the first and second portions 185, 186 are located on opposite sides of the central portion 187. As seen in the figures, the central portion 187 has a reduced thickness relative to the first and second portions 185, 186. Thus, the coupling member 162 may be flexible and capable of bending about the central portion 187 thereof.

The coupling member 162 extends from a first end 188 to a second end 189. The first portion 185 of the coupling member 162 comprises the first end 188 and the second portion 186 of the coupling member 162 comprises the second end 189. The first end 188 of the coupling member 162 comprises an opening 190 therein that leads into an internal cavity 192. The coupling member 162 is coupled to the motor 160 by inserting a shaft 191 of the motor 160 through the opening 190 in the first end 188 of the coupling member 162 and into the internal cavity 192. Thus, the shaft 191 of the motor 160 nest within the internal cavity 192. The shaft 191 of the motor 190 is preferably in surface contact with the coupling member 162 so that rotation of the shaft 191 of the motor 190 results in rotation of the coupling member 162, which in turn results in rotation of the eccentric 161 due to its coupling to the second portion 186 of the coupling member 162. Specifically, in the exemplified embodiment there is a tight fit engagement, such as an interference fit, between the shaft 191 and the walls surrounding the internal cavity 192 that causes the coupling member 162 to rotate as the shaft 191 rotates. Of course, other techniques for coupling the shaft 191 to the coupling member 162 are possible, including engaging mechanical features on each, using hardware, welding, or the like. The coupling member 162 and the motor 160 may be detachably coupled together in some embodiments such that the shaft 191 can be readily inserted into and removed from the opening 190 (i.e., such as when the exemplary interference fit is used to couple those two components together).

As best seen in FIG. 14, the eccentric 161 comprises a peg-like portion 193 extending from the first flange 181. The peg-like portion 193 is located within an internal cavity 194 in the second portion 186 of the coupling member 162 to couple the eccentric 161 to the coupling member 162. The coupling member 162 comprises a top portion 195 that is located between the first and second flanges 180, 181 of the eccentric 161 so that the coupling between the eccentric 161 and the coupling member 162 is quite secure. The top portion 195 of the coupling member 162 is directly adjacent and in contact with the second flange 181 of the eccentric. In fact, in this embodiment the second flange 181 is located within a recess 196 of the coupling member 162 that is formed into the second portion 186 of the coupling member 162. The top portion 195 of the coupling member 162 is the portion located between the recess 196 and the second end 189 of the coupling member 162. As a result of this engagement between the eccentric 161 and the coupling member 162, although the motor 160 and the coupling member 162 can be quite easily separated from one another, the same is not true of the eccentric 161 and the coupling member 162. The eccentric 161 and the coupling member 162 may be coupled together so as to operate as a single component despite the fact that they might be formed from different materials. Of course, in other embodiments the eccentric 161 and the coupling member 162 may be more readily detached from one another if this is desired.

Thus, the coupling of the motor 160, the coupling member 162, the eccentric 161, and the guide pin 170 should now be fully understood. Specifically, the second portion 172 of the guide pin 170 is embedded within the material of the stem 120 and the first portion 171 of the guide pin 170 extends into and is suspended within the inner cavity 122 of the stem 120. The eccentric 161 is placed next within the inner cavity 122 such that it is translated axially into the inner cavity 122 until the first portion 171 of the guide pin 170 extends into and through the aperture 166 formed into the second end 198 of the eccentric 161. The first portion 171 of the guide pin 170 nests within the depression 184 of the eccentric 161. The eccentric 161 is coupled directly to the coupling member 162, which in turn is coupled directly to the shaft 191 of the motor 190. Thus, when the motor is activated, the shaft 191 rotates about an axis, which in turn causes the coupling member 162 to rotate about the axis, which in turn causes the eccentric 161 to rotate about the axis. Due to the off-center positioning of the main body 167 of the eccentric 161, rotation of the eccentric 161 creates vibrations that are felt within the head portion 220 and the tooth cleaning elements 215 of the oral care implement 1000. The eccentric 161 is maintained in central position within the inner cavity 122 due to its engagement with the first portion 171 of the guide pin 170 as described herein. Specifically, the guide pin 170 prevents the eccentric 161 from bumping up against the inner surface 123 of the stem 120 when the eccentric 161 is rotating.

In certain aspects, the invention described herein may be directed to a method of manufacturing the handle 100 of the oral care implement 1000, specifically with regard to the manner in which the guide pin 170 becomes embedded within the stem 120. In such a method, first the gripping portion 110 of the handle 100 is formed and provided. Next, a mold that defines a mold cavity having a shape that corresponds to a shape of the stem 120 of the handle 100 is provided. Next, the guide pin 170 is supported so that the second portion 172 of the guide pin 170 is located within the mold cavity. At this point, a first material may be injected into the mold cavity so that the first material surrounds the second portion 172 of the guide pin 170 and fills in the entirety of the mold cavity. Upon cooling, the first material hardens to form the stem 120 of the handle 100 and the second portion 172 of the guide pin 170 becomes embedded within the upper portion 142 of the stem 120. Furthermore, a first portion 171 of the guide pin 170 that was not previously located within the mold cavity extends into the inner cavity 122 of the stem 120. Next, the vibratory element 199, which may comprise the motor 160, the eccentric 161, and possibly also the coupling member 162, are inserted into the inner cavity 122 of the stem 120 until the first portion 171 of the guide pin 170 extends into the aperture 166 in the second end 198 of the eccentric 161. Finally, the stem 120 is coupled to the gripping portion 110 to form the handle 100 in the manner described herein. At some point during this method, the electronics component 150 is inserted into the handle 100 and electrically coupled to the motor 160.

Figure 15:
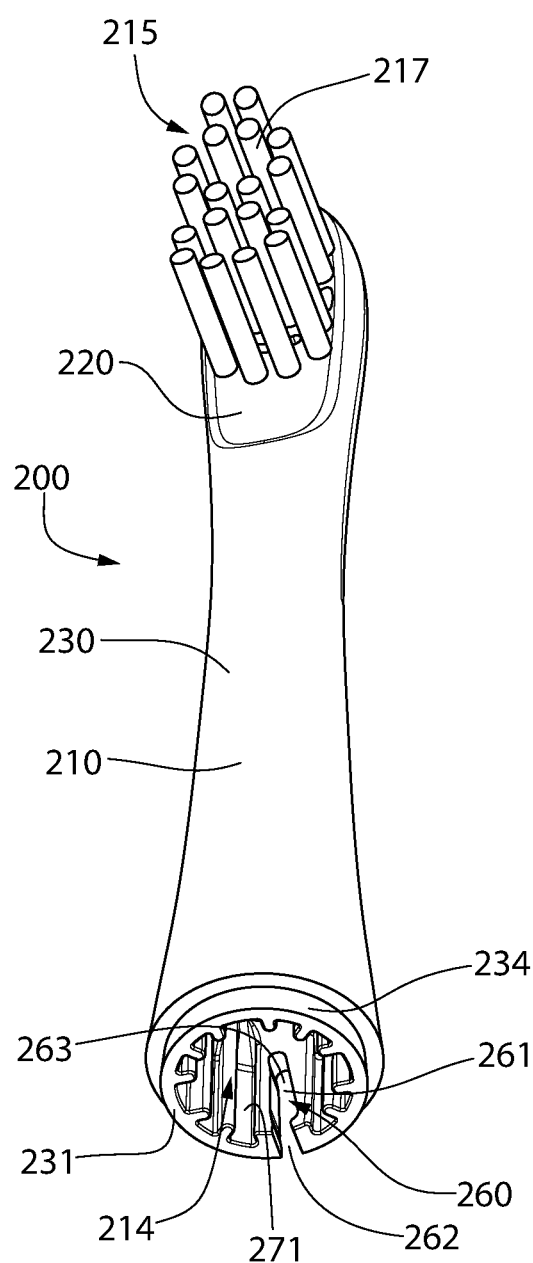
FIG. 15 is a front perspective view of a first component of the replacement head of FIG. 4, a second component of the replacement head having been removed.
Figure 16:
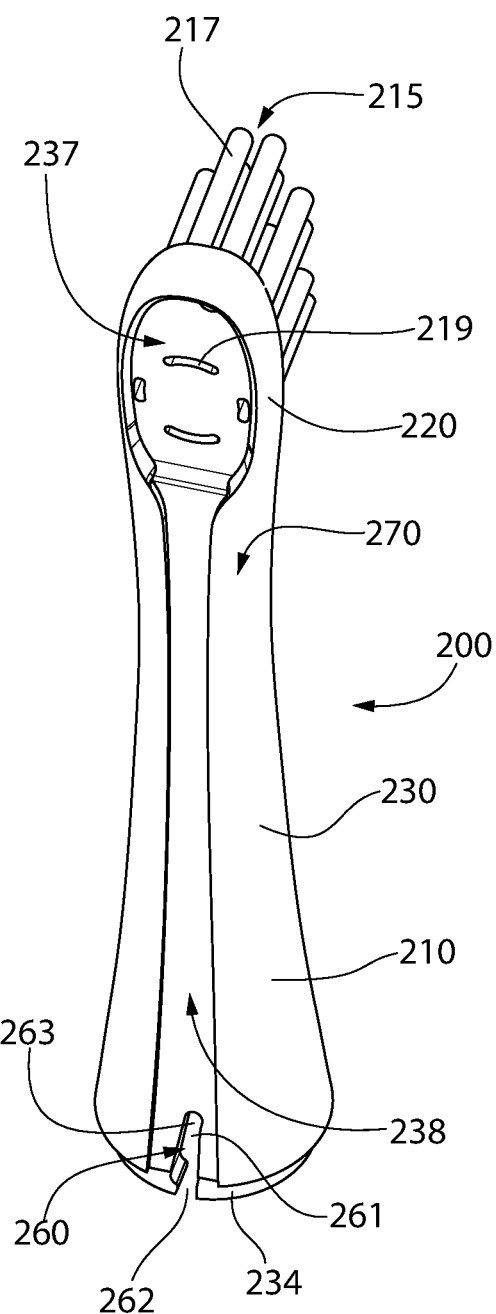
FIG. 16 is a rear perspective view of the first component of the replacement head of FIG. 15.

The replacement head 200 will now be described herein with reference to FIGS. 5, 15, and 16 concurrently. FIGS. 15, and 16 illustrate the replacement head 200 with the second component 240 thereof omitted. Thus, FIGS. 15 and 16 illustrate only the first component 230 (i.e., the rigid material or hard plastic) of the replacement head 200 and omit the second component (i.e., the resilient or elastomeric material) of the replacement head 200. It should be noted that in some embodiments the first component 230 is a body of the replacement head 200 and the second component 240 is an elastomeric material that is overmolded onto the body. The first component 230 forms the structural skeleton or backbone of the replacement head 200 including portions of the sleeve portion 210 and the head portion 220 of the replacement head 200. The first component 230 of the replacement head 200 comprises the annular recess 234 at its bottom end, a basin 237 formed into the head portion 220, and an elongated channel 238 that extends from the annular recess 234 to the basin 237. The annular recess 234, the elongated channel 238, and the basin 237 form a continuous depressed portion of the first component 230 of the replacement head 200.

Furthermore, the replacement head 200 comprises a locking element 260 that is configured to mate with a locking element 290 (FIG. 19) of the handle 100. In the exemplified embodiment, the locking element 260 comprises a slot 261 that is formed into the first component 230. The slot 261 extends entirely through the first component 230 of the replacement head 200 from an outer surface 270 of the first component 230 to an inner surface 271 of the first component 230. Furthermore, the slot 261 is elongated axially from the bottom edge 231 of the first component 230 in a direction generally towards the head portion 220. A first portion 262 of the slot 261 is located along the annular recess 234 of the first component 230 and a second portion 263 of the slot 261 is located along the elongated channel 238 of the first component 230. Thus, the slot 261 has a length that is greater than the length of the annular recess 234 but because the slot 261 is also aligned with the elongated channel 238 the entirety of the slot 261 is formed into a portion of the first component 230 of the replacement head 200 that has a reduced thickness relative to the remainder of the first component 230 of the replacement head 200.

Figure 5:
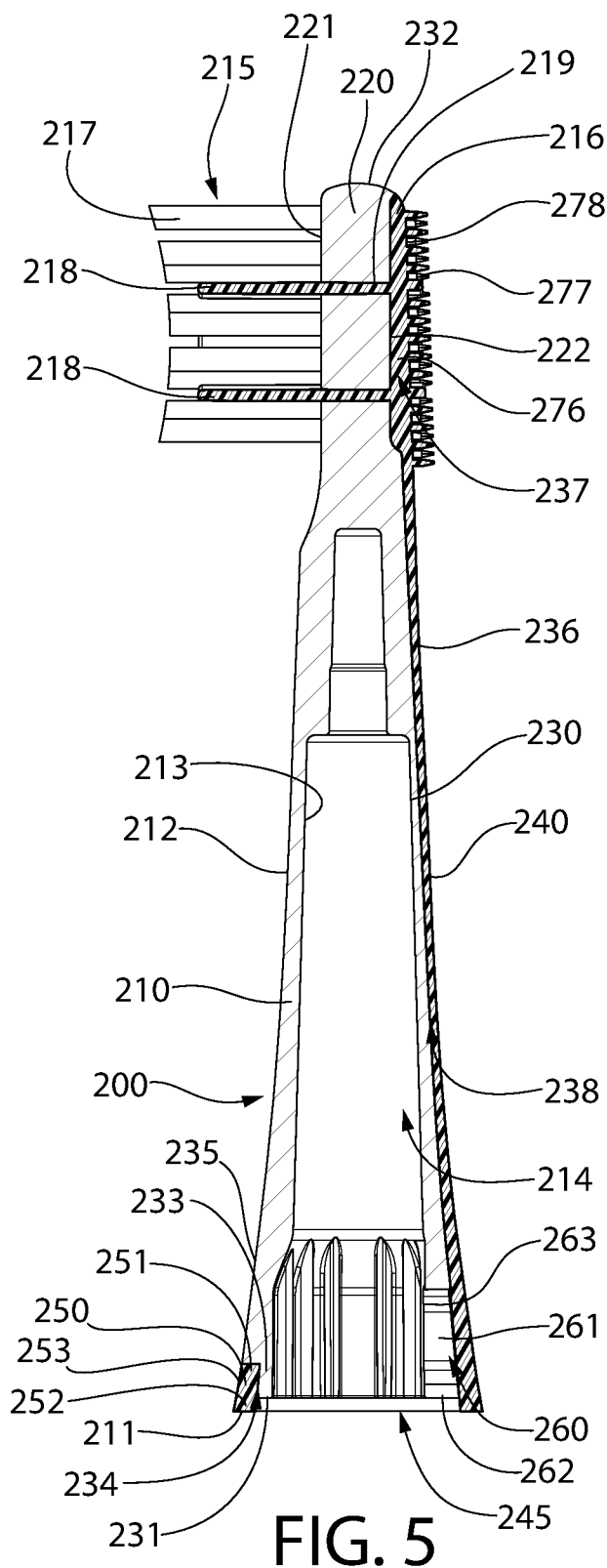
FIG. 5 is a cross-sectional view taken along line IV-IV of FIG. 4.
Figure 17:
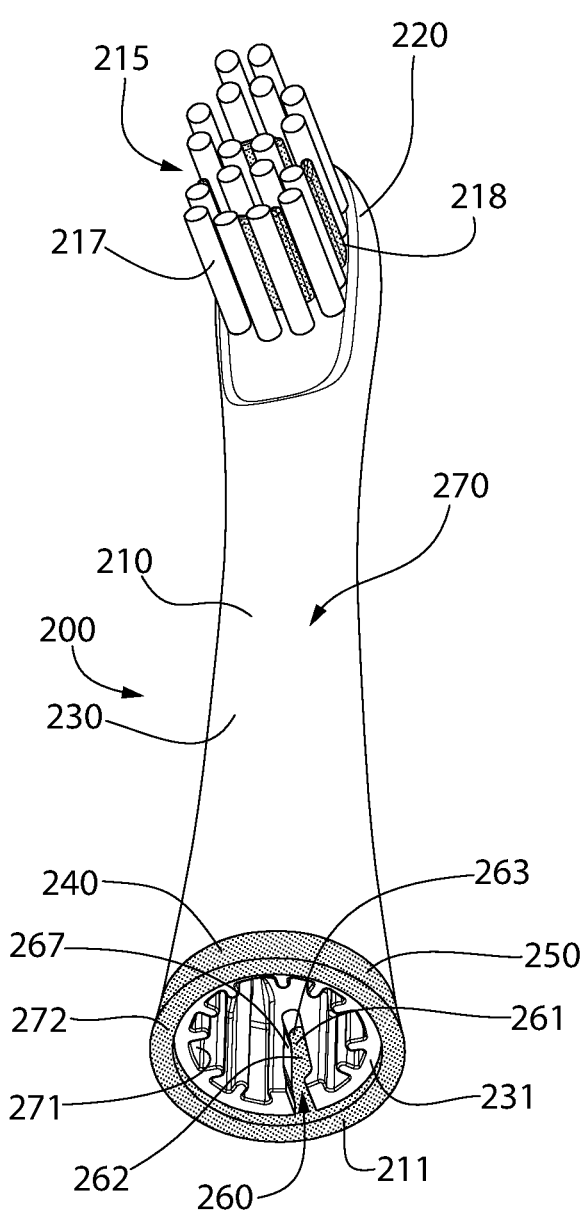
FIG. 17 is a front perspective view of the replacement head of FIG. 4 including both the first and second components.
Figure 18:
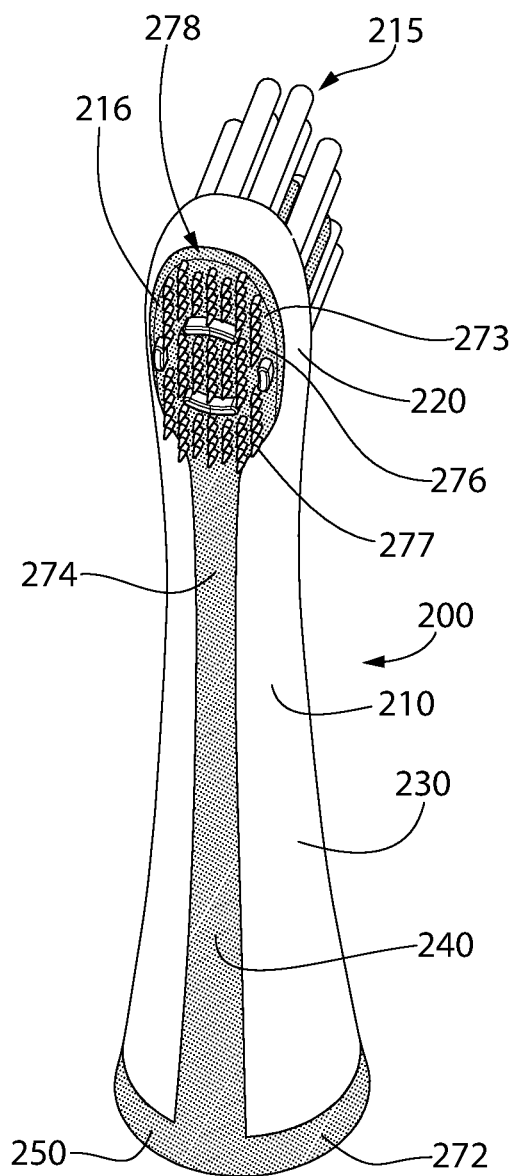
FIG. 18 is a rear perspective view of the replacement head of FIG. 17.

Referring to FIGS. 5, 17, and 18, the replacement head 200 will be further described. FIGS. 5, 17, and 18 illustrate the entire replacement head 200 including the first component 230 and the second component 240. As has been described herein, in certain embodiments the first component 230 is a rigid material such as a hard plastic and the second component 240 is a resilient or elastomeric material such as a thermoplastic elastomer. The second component 240 is preferably injection molded onto the first component 230 so that the second component 240 forms an integral mass of elastomeric or resilient material that fills in the annular recess 234, the elongated channel 238, and the basin 237. Thus, the second component 240 forms in integral mass of elastomeric material comprising a first portion 272 that forms the annular ring 250, a second portion 273 that forms the soft tissue cleaner 216, and a third portion 274 that is disposed within the elongated channel 238.

The second portion 273 of the integral mass of elastomeric material that forms the soft tissue cleaner 216 comprises a pad portion 276 disposed within the basin 237 and a plurality of protuberances or nubs 277 extending from an outer surface 278 of the pad portion 276. The third portion 274 of the integral mass of elastomeric material connects the first portion 272 to the second portion 273 (i.e., connects the annular ring 250 to the soft tissue cleaner 216). Furthermore, in the exemplified embodiment the integral mass of elastomeric material also comprises a fourth portion 275 that forms the resilient cleaning elements 218 extending from the head portion 220. Specifically, the integral mass of elastomeric material extends through the passageways 219 in the head portion 220 to form both the soft tissue cleaner 216 on the rear surface 222 of the head portion 220 and the resilient cleaning elements 218 extending from the front surface 221 of the head portion 220.

As can be seen in FIGS. 5, 17, and 18, the elastomeric material of the second component 240 forms a surface of the slot 261 of the locking element 260. Specifically, as noted above the first portion 262 of the slot 261 is located along the annular recess 234 and the second portion 263 of the slot 261 is located along the elongated channel 238. Furthermore, the elastomeric material of the second component 240 is disposed within annular recess 234 and the elongated channel 238. Thus, the elastomeric material of the second component 240 passes directly over the slot 261 and forms a boundary wall of the slot 261. Thus, the slot 261 is defined in its entirety by a portion of the second component 240 that covers the slot 261 and a wall 267 of the first component 230 that extends between the inner and outer surfaces 270, 271 of the first component 230. Although the second component 240 passes over and covers the slot 261, it does not penetrate into the slot 261 and thus the slot 261 remains as an opening that is free of elastomeric material. The elastomeric material of the second component 240 merely forms one of the boundaries of the slot 261.

When viewed from the outside, the second component 240 covers the slot 261 in its entirety so that the slot 260 is not at all visible to a user or consumer. Instead, a consumer or user will only see the outer surface of the first component 230 and the second component 240 when viewing the replacement head 200. Thus, the locking element 260 is not visible or exposed at an outer surface of the replacement head 200. This is aesthetically beneficial in addition to any functional benefits that have been described herein.

Thus, the slot 261 is closed at the outer surface 270 of the first component 230 and open at the inner surface 271 of the first component 230. This enables the slot 261 to be accessible by a locking element (i.e., locking protuberance) on the stem 120 of the handle 100 despite the slot 261 being covered and therefore not visible when the replacement head 200 is viewed by a user or consumer.

As noted previously, the annular ring 250 formed by the first portion 272 of the second component 240 extends beyond the bottom edge 231 of the first component 230 without covering the bottom edge 231 of the first component 230. This is important because the slot 261 is open at the bottom edge 231 of the first component 230 to enable a locking protuberance on the stem 120 of the handle 100 to pass into and nest within the slot 261. Thus, the elastomeric material of the second component 240 cannot cover the opening at the bottom edge 231 of the first component 230 that leads into the slot 261.

Figure 19:
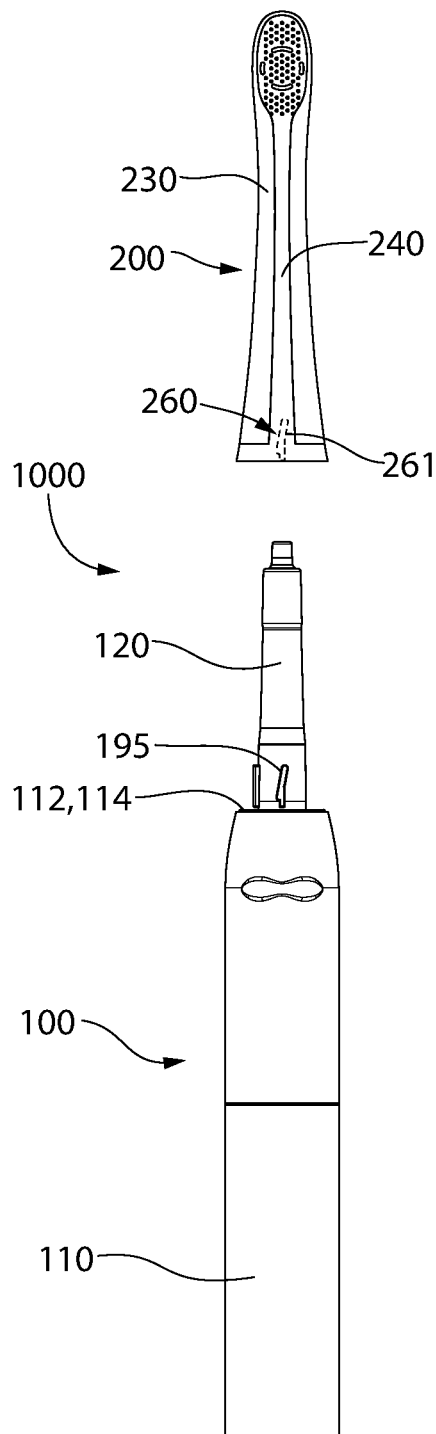
FIG. 19 is a rear view of the oral care implement of FIG. 1 with the replacement head detached from the handle.
Figure 20:
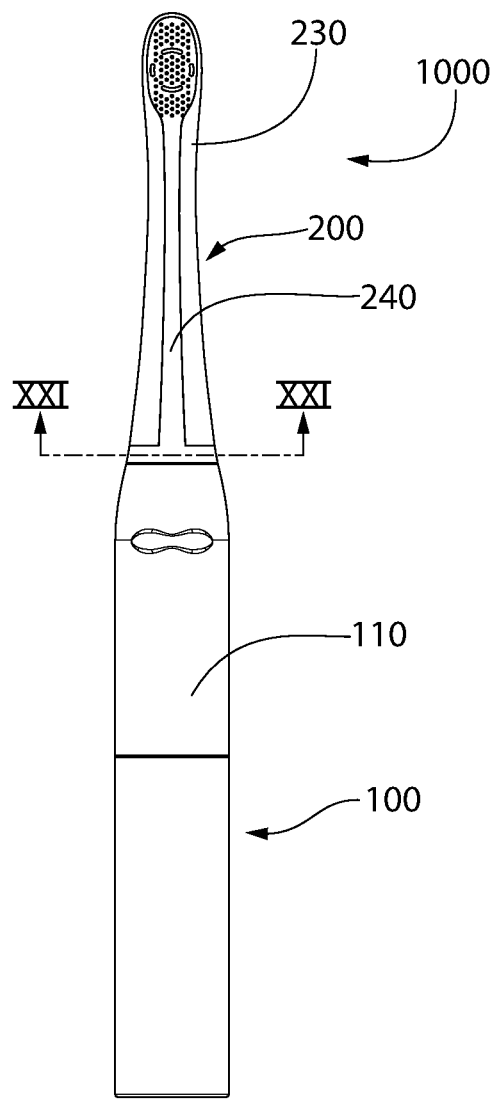
FIG. 20 is a rear view of the oral care implement of FIG. 1 with the replacement head coupled to the handle.
Figure 21:
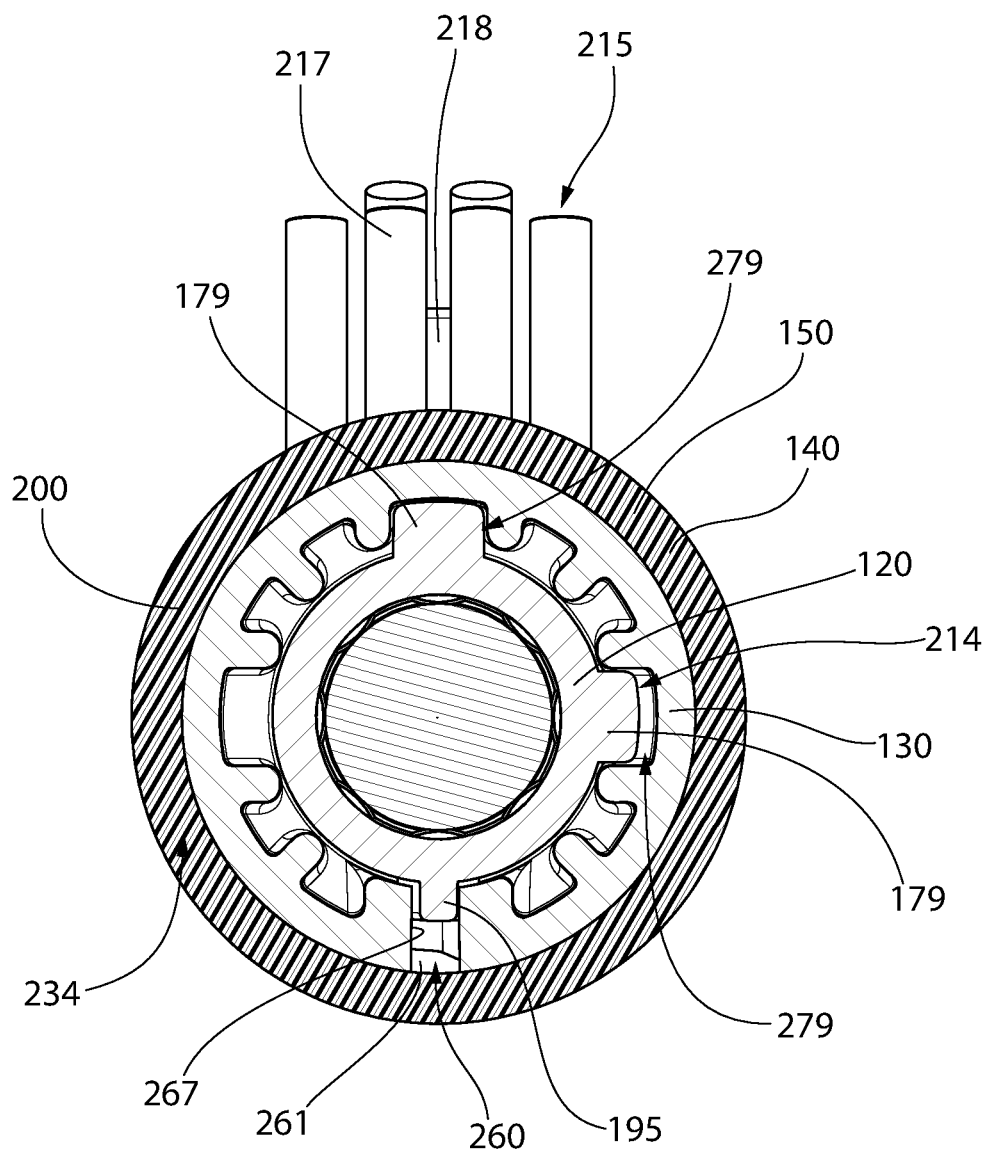
FIG. 21 is a cross-sectional view taken along line XXI-XXI of FIG. 20.

Referring to FIGS. 19-21 concurrently, the oral care implement 1000 is illustrated with the replacement head 200 detached from the handle 100 (FIG. 19) and with the replacement head 200 attached to the handle 100 (FIG. 20). The handle 100 comprises a locking protuberance 197 protruding from the stem 120 adjacent the distal end 112/shoulder 114 of the gripping portion 110. Furthermore, the locking element 260 (i.e., the locking slot 261) is illustrated in phantom in FIG. 19 because it is hidden from view due to it being covered by the elastomeric material of the second component 240.

When the replacement head 200 is coupled to the handle 100, the stem 120 of the handle 100 is located within the cavity 214 of the replacement head 200. Furthermore, the locking protuberance 195 extending from the stem 120 is located within the locking slot 261 of the replacement head 200. Thus, before the replacement head 200 can be coupled to the handle 100, the locking element 260 (locking slot 261) of the replacement head 200 must be axially aligned with the locking protuberance 195 of the stem 120. As the replacement head 200 is translated onto the stem 120, the locking protuberance 195 enters into and becomes nested within the locking slot 261. The locking element/locking slot 260, 261 and the locking protuberance 195 have mating features that engage one another to lock the replacement head 200 to the handle 100. The engagement between the locking protuberance 195 and the locking slot 261 is sufficiently strong so that the oral care implement 1000 can be held upside-down (with the head portion 220 facing the ground) without the replacement head 200 becoming detached from the handle 100. However, a relatively minor pull on the replacement head 200 relative to the handle 100 will cause the replacement head 200 to become detached and separated from the handle 100. The stem 120 may also include alignment ribs 179 that nest within alignment channels 279 of the replacement head 200 when the replacement head 200 is coupled to the handle 100 to facilitate proper alignment of the replacement head 200 relative to the handle 100.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
  a handle having a longitudinal axis and comprising:
    a gripping portion extending from a proximal end to a distal end; and
    a stem extending from the distal end of the gripping portion, the stem having an inner cavity defined by an inner surface and an upper wall;
  a vibratory element at least partially located in the stem and operably coupled to a power source, the vibratory element comprising a motor and an eccentric, the eccentric having a first end that is operably coupled to the motor and a second end opposite the first end, the second end comprising an aperture;
  a guide pin fixed to the stem, a first portion of the guide pin protruding from the upper wall and into the inner cavity of the stem and extending through the aperture in the second end of the eccentric; and
  a replacement head comprising a sleeve portion having a cavity, wherein the replacement head is detachably coupled to the handle with the stem of the handle located within the cavity of the sleeve portion;
  wherein the guide pin is axially and rotationally fixed relative to the stem such that the guide pin is non-movable relative to the stem.

2. The oral care implement according to claim 1 wherein the stem comprises an upper portion located between the upper wall of the stem and a distal end of the stem, the guide pin comprising a second portion that is embedded within the upper portion of the stem to fix the guide pin to the stem.

3. The oral care implement according to claim 1 wherein the eccentric comprises a main body extending along an axis from a first end to a second end and a first flange extending transversely from the second end of the main body, the first flange forming the second end of the eccentric.

4. The oral care implement according to claim 3 wherein the main body of the eccentric comprises an inner surface and an outer surface opposite the inner surface, a depression formed into the inner surface of the main body and extending axially from the second end of the main body towards the first end of the main body.

5. The oral care implement according to claim 4 wherein at least a portion of the first portion of the guide pin nests within the depression in the inner surface of the main body of the eccentric.

6. The oral care implement according to claim 3 further comprising a second flange extending from the first end of the main body of the eccentric, each of the first and second flanges extending transversely from the inner surface of the eccentric in a direction away from the outer surface of the eccentric.

7. The oral care implement according to claim 6 further comprising a coupling member that is coupled directly to a shaft of the motor and the second flange of the eccentric.

8. The oral care implement according to claim 7 wherein the coupling member is formed of a plastic material, the coupling member having a central portion with a reduced thickness relative to a remainder of the coupling member.

9. The oral care implement according to claim 7 wherein the coupling member comprises a first portion and a second portion located on opposite sides of the central portion, the first portion comprising an internal cavity and forming a first end of the coupling member, the shaft of the motor positioned within the internal cavity of the first portion of the coupling member.

10. The oral care implement according to claim 9 wherein the second flange of the eccentric nests within a recess formed into the second portion of the coupling member so that a top of the second portion of the coupling member is located between the first and second flanges of the eccentric.

11. An oral care implement comprising:
  a handle having a longitudinal axis and comprising:
    a gripping portion extending from a proximal end to a distal end; and
    a stem extending from the distal end of the gripping portion, the stem having an inner cavity defined by an inner surface and an upper wall;
  a vibratory element at least partially located in the stem and operably coupled to a power source, the vibratory element comprising a motor and an eccentric, the eccentric having a first end that is operably coupled to the motor and a second end opposite the first end, the second end comprising an aperture;

a guide pin fixed to the stem, a first portion of the guide pin protruding from the upper wall and into the inner cavity of the stem and extending through the aperture in the second end of the eccentric; and a replacement head comprising a sleeve portion having a cavity, wherein the replacement head is detachably coupled to the handle with the stem of the handle located within the cavity of the sleeve portion;

wherein the stem comprises an upper portion located between the upper wall of the stem and a distal end of the stem, the guide pin comprising a second portion that is embedded within the upper portion of the stem to fix the guide pin to the stem;

wherein the guide pin comprises a main body that is elongated along an axis and at least one ring-like protrusion extending from the main body along the second portion of the guide pin.

12. The oral care implement according to claim 11 wherein the at least one ring-like protrusion comprises a first ring-like protrusion and a second ring-like protrusion that are axially spaced apart along the second portion of the guide pin.

13. A handle for an electric toothbrush, the handle comprising:
a gripping portion;
a stem extending from the gripping portion, the stem comprising an inner cavity;
a vibratory element at least partially located in the stem and operably coupled to a power source, the vibratory element comprising a motor and an eccentric, the eccentric having a first end that is coupled to the motor and a second end opposite the first end, the second end comprising an aperture; and
a guide pin fixed to the stem, the guide pin comprising a first portion and a second portion, the second portion of the guide pin embedded within a wall of the stem and the first portion of the guide pin suspended within the inner cavity of the stem and extending through the aperture in the second end of the eccentric.

14. The oral care implement according to claim 13 wherein the guide pin comprises a main body that is elongated along an axis from a first end to a second end and at least one ring-like protrusion extending from the main body along the second portion of the guide pin.

15. The oral care implement according to claim 14 wherein the eccentric comprises a first flange extending transversely from the second end of the main body, the first flange forming the second end of the eccentric.

16. The oral care implement according to claim 15 wherein the main body of the eccentric comprises an inner surface having an elongated depression formed therein, the elongated depression extending axially from the second end of the main body towards the first end of the main body, wherein at least a portion of the first portion of the guide pin nests within the depression in the inner surface of the main body of the eccentric.

17. A method of manufacturing a handle of an electric toothbrush, the method comprising:
providing a gripping portion of the handle;
providing a mold that defines a mold cavity, the mold cavity corresponding to a stem of the handle;
supporting a second portion of a guide pin within the mold cavity;
injecting a first material into the mold cavity so that the first material surrounds the second portion of the guide pin, wherein upon cooling the first material hardens to form the stem of the handle with the second portion of the guide pin being embedded within the stem and a first portion of the guide pin suspended within a cavity of the stem;
inserting a vibratory element into the cavity of the stem until the first portion of the guide pin extends into an aperture in a distal end of the vibratory element; and
coupling the stem to the gripping portion so that at least a portion of the stem extends from a distal end of the gripping portion.

18. The method according to claim 17 wherein the gripping portion of the handle comprises a first part and a second part that are configured to be coupled together, the second part of the gripping portion comprising:
a cavity;
a first end having a first opening providing a passageway into the cavity; and
a second end having a second opening providing a passageway into the cavity.

19. The method according to claim 18 wherein coupling the stem to the gripping portion comprises inserting the stem through the first opening in the first end of the second part of the gripping portion, into the cavity of the second part of the gripping portion, and through the second opening in the second end of the second part of the gripping portion until the portion of the stem protrudes from the second end of the second part of the gripping portion, and further comprising coupling the first and second parts of the gripping portion together.

* * * * *